(12) United States Patent
Dambinova

(10) Patent No.: US 7,622,114 B2
(45) Date of Patent: *Nov. 24, 2009

(54) ASSAY METHODS FOR IMMEDIATE DIAGNOSIS OF CAUSE OF STROKE

(75) Inventor: Svetlana A. Dambinova, Atlanta, GA (US)

(73) Assignee: CIS Biotech, Inc., Atlanta, GA (US)

(*) Notice: Subject to any disclaimer, the term of this patent is extended or adjusted under 35 U.S.C. 154(b) by 122 days.

This patent is subject to a terminal disclaimer.

(21) Appl. No.: 11/339,440

(22) Filed: Jan. 25, 2006

(65) Prior Publication Data

US 2006/0172341 A1 Aug. 3, 2006

Related U.S. Application Data

(63) Continuation of application No. 11/076,074, filed on Mar. 9, 2005, which is a continuation of application No. 09/922,011, filed on Aug. 2, 2001, now Pat. No. 6,896,872.

(60) Provisional application No. 60/301,297, filed on Jun. 27, 2001.

(51) Int. Cl.
*A61K 39/395* (2006.01)
*A61K 49/00* (2006.01)
*G01N 33/53* (2006.01)
*G01N 33/00* (2006.01)

(52) U.S. Cl. .................. 424/139.1; 435/7.1; 435/7.95; 530/387.1; 424/9.1

(58) Field of Classification Search ............... None
See application file for complete search history.

(56) References Cited

U.S. PATENT DOCUMENTS 5,849,895 A 12/1998 Daggett et al.
6,316,611 B1 11/2001 Daggett et al.
6,896,872 B2 5/2005 Dambinova
2005/0181466 A1 8/2005 Dambinova et al.
2006/0024749 A1 2/2006 Dambinova

FOREIGN PATENT DOCUMENTS

WO WO 02/12892 A2 2/2002
WO WO 2006/081188 A1 8/2006
WO WO 2006/135893 A2 12/2006

OTHER PUBLICATIONS

Dambinova et al. Journal of Stroke and Cerebrovascular Disease, 10:A1 [abstract] Jul. 2001.*
Moonis and Fisher, Cerebrovascular Diseases, 11(3): 143-150, May/Jun. 2000.*
Altura et al. Neuroscience Letters 230:37-40 (1997).*
Söderberg et al. Stroke 30: 328-337 (1999).*
DeGiorgio et al., Nature Medicine, 7(11):1189-1193, 2001.*
Omdal et al., European Journal of Neurology, 12:392-398, 2005.*
U.S. Appl. No. 11/076,074, Dambinova.

U.S. Appl. No. 11/339,452, Dambinova.
U.S. Appl. No. 11/338,447, Dambinova.
U.S. Appl. No. 11/451,679, Dambinova.
Dambinova, et al., "Autoantibodies to Subtypes of Glutamate Receptors as a Hallmarks of Brain Damage: Diagnostic Significance for Paroxysmal Activity and Ischemia." *Journal of Higher Nervous Activity*. 1997. vol. 47(2), pp. 151-156.
Gusev, et al., "Neuroprotective Effects of Glycine for Therapy of Acute Ischaemic Stroke." *Cerebrovasc Dis 2000*; 10:49-60.
Dambinova, et al., "Monitoring of Brain Spiking Activity and Autoantibodies to N-Terminus Domain of GluR1 Subunit of AMPA Receptors in Blood Serum of Rats with Cobalt-Induced Epilepsy." *Journal of Neurochemistry*, Lippincott-Raven Publishers, Philadelphia.
Dambinova, et al., "The presence of autoantibodies to N-terminus domain of GluR1 subunit of AMPA receptor in the blood serum of patients with epilepsy." *Journal of Neurological Sciences*, 152 (1997) 93-97.
Meldrum, B.S., "Glutamate as a Neurotransmitter in the Brain: Review of Physiology and Pathology$^{mt;epmub1ubxmx}$" *Journal of Nutrition*. 2000; 130:1007S-1015S.
Monyer et al., "Heteromeric NMDA Receptors ..." *Science* May 22, 1992; 256:1217-1221.
Dambinova et al., "Blood Test Detecting Autoantibodies ..." *Clinical Chemistry* 2003 49(10); 1181-1182.
Castillo, J., et al., "Neuroexcitatory Amino Acids and Their Relation to Infarct Size and Neurological Deficit in Ischemic Stroke," *Stroke*, 27(6):1060-1065 (Jun. 1996).
Castillo, J., et al., "Progression of ischaemic stroke and excitotoxic aminoacids," *Lancet*, 349(9045):79-83 (Jan. 11, 1997).
Dambinova, S.A., et al., "Autoantibodies to Subtypes of Glutamate Receptors as a Hallmarks of Brain Damage: Diagnostic Significance for Paroxysmal Activity and Ischemia,"*J. Higher Nervous Activity*, 47 (2):151-156 (1997) (transl. of: *Zh. Vyssh. Nerv. Deiat. Im. I. P. Pavlova*, 47(2):439-446 (Mar.-Apr. 1997).
Dambinova, S.A., et al., "Blood test detecting autoantibodies to N-methyl-D-aspartate neuroreceptors for evaluation of patients with transient ischemic attack and stroke," *Clinical Chemistry*, 49(10):1752-1762 (2003).

(Continued)

*Primary Examiner*—John D. Ulm
*Assistant Examiner*—Stacey MacFarlane
(74) *Attorney, Agent, or Firm*—Clark G. Sullivan; Geoffrey K. Rogers; Arnall Golden Gregory

(57) ABSTRACT

A methods, kits and compositions for diagnosing a central nervous system disorder, particularly transient ischemic attack or stroke, comprising measuring the level of NR2A and/or NR2B NMDA receptor or fragment thereof, in a biological sample from a human subject, and optionally measuring other biomarkers such as homocysteine and glutamate. The method is particularly useful for identifying individuals that are at risk for stroke, and for diagnosing stroke in an emergency room setting.

11 Claims, No Drawings

OTHER PUBLICATIONS

Dambinova, S.A., et al., "Monitoring of Brain Spiking Activity and Autoantibodies to N-Terminus Domain of GluR1 Subunit of AMPA Receptors in Blood Serum of Rats with Cobalt-Induced Epilepsy," *J. Neurochem.*, 72(3):2088-2093 (Nov. 1998).

Dambinova, S.A., et al., "Multiple panel of biomarkers for TIA/ stroke evaluation," *Stroke*, 33(5):1181-1182 (May 2002).

Dambinova, S.A., et al., "The presence of autoantibodies to N-terminus domain of GluR1 subunit of AMPA receptor in the blood serum of patients with epilepsy." *J. Neurological Sciences*, 152(1): 93-97 (Nov. 6, 1997).

Davalos, A., et al., "Duration of Glutamate Release After Acute Ischemic Stroke," *Stroke*, 28(4): 708-710 (Apr. 1997).

Dávalos, A., et al., "Neurological Deterioration in Acute Ischemic Stroke: Potential Predictors and Associated Factors in the European Cooperative Acute Stroke Study (ECASS) 1." *Stroke*, 30(12): 2631-2636 (Dec. 1999).

Gahring, L.C.,, et al., "Autoantibodies to Neuronal Glutamate Receptors in Patients with Paraneoplastic Neurodegenerative Syndrome Enhance Receptor Activation," *Molec. Medicine*, 1(3): 245-253 (Mar. 1995).

Gray, J.J., et al., "Evaluation of a commercial latex agglutination test for detecting antibodies to cytomegalovirus in organ donors and transplant recipients," *J. Virol. Meth.*, 16(1-2): 13-19 (May 1987).

Gusev, E.L., et al., "Investigation of the Level of Autoantibodies to Glutamate Receptors in Blood Serum of Patients in Acute Period of Ischemic Stroke," *Zhurnal Nevrologii I Psikhiatrii Imeni S. S. Korsakova*; 96(5):68-72 (1996) (in Russian; Abstract in English).

Gusev, E.L., et al., "Neuroprotective Effects of Glycine for Therapy of Acute Ischaemic Stroke," *Cere-brovasc. Dis.*, 10(1):49-60 (Jan.-Feb. 2000).

Hess, S.D., et al.; "Cloning and Functional Characterization of Human Heteromeric N-Methyl-D-Aspartate Receptors," *J. Pharmacol. Exp. Ther.*, 278(2): 808-816 (Aug. 1996); XP000676640; Abstract.

Hill, M.D., et al., "Biochemical markers in acute ischemic stroke," *Canadian Medical Association Journal*,; 162:1139-1140 (Apr. 18, 2000).

Lipton, S.A., et al., "Neurotoxicity associated with dual actions of homocysteine at the N-methyl-D-aspartate receptor," *Proc. Natl. Acad. Sci. USA*, 94(11):5923-5928 (May 27, 1997).

Meldrum, B.S., "Glutamate as a Neurotransmitter in the Brain: Review of Physiology and Pathology," *J. Nutrition*, 130:1007S-1015S (2000).

Monyer, H., et al., "Heteromeric NMDA Receptors: Molecular and Functional Distinction of Subtypes," *Science*, 256(5060):1217-1221; (May 22, 1992).

Pang, S.C., et al., "Early diagnosis of acute myocardial infarction by myoglobin latex agglutination test," *Jpn. Heart J.*, 29(5):631-638 (Sep. 1988).

Rogers, S.W., "Autoantibodies to Glutamate Receptor G1uR3 in Rasmussen's Encephalitis," *Science*, 265(5172):648-651 (Jul. 29, 1994).

Senju, O., et al., "A new immuno quantitative method by latex agglutination—application for the determination of serum C-reactive protein (CRP) and its clinical significance," *J. Clin. Lab. Immunol.*, 19(2): 99-103 (Feb. 1986).

Skoromets, A.A., et al.; [Autoantibodies to NMDA-type glutamate receptors in the blood of patients with acute ischemic and hemorrhagic stroke] *Zh. Nevrol. Psikhiatr. Im. S. S. Korsakova* [*J. Neurological Sciences*], 97(6):53-58 (1997) (In Russian, Abstract in English).

Vila,N., et al., "Plasma homocysteine levels in patients with ischemic cerebral infarction," *Med. Clin.* (Barcelona) 110(16): 605-608 (May 9, 1998). (In Spanish) Provided as abstract in English.

Vincent, A., et al., "Pathogenic autoantibodies to neuronal proteins in neurological disorders," *J. Neuroimmunology*, 100(1-2):169-180 (Dec. 1999).

Yamamoto, T., et al., "CSF and ECF Gluatmate Concentrations in Head Injured Patients," *Acta Neurochir.* [Suppl] 75:17-19 (1999).

\* cited by examiner

SEQUENCE LISTING

```
<160> NUMBER OF SEQ ID NOS: 17

<210> SEQ ID NO 1
<211> LENGTH: 1464
<212> TYPE: PRT
<213> ORGANISM: homo sapiens

<400> SEQUENCE: 1

Met Gly Arg Leu Gly Tyr Trp Thr Leu Leu Val Leu Pro Ala Leu Leu
1               5                   10                  15

Val Trp Arg Asp Pro Ala Gln Asn Ala Ala Ala Glu Lys Gly Pro Pro
                20                  25                  30

Ala Leu Asn Ile Ala Val Leu Leu Gly His Ser His Asp Val Thr Glu
            35                  40                  45

Arg Glu Leu Arg Asn Leu Trp Gly Pro Glu Gln Ala Thr Gly Leu Pro
        50                  55                  60

Leu Asp Val Asn Val Val Ala Leu Leu Met Asn Arg Thr Asp Pro Lys
65                  70                  75                  80

Ser Leu Ile Thr His Val Cys Asp Leu Met Ser Gly Ala Arg Ile His
                85                  90                  95

Gly Leu Val Phe Gly Asp Asp Thr Asp Gln Glu Ala Val Ala Gln Met
                100                 105                 110

Leu Asp Phe Ile Ser Ser Gln Thr Phe Ile Pro Ile Leu Gly Ile His
            115                 120                 125

Gly Gly Ala Ser Met Ile Met Ala Asp Lys Asp Pro Thr Ser Thr Phe
        130                 135                 140

Phe Gln Phe Gly Ala Ser Ile Gln Gln Gln Ala Thr Val Met Leu Lys
145                 150                 155                 160
```

```
Ile Met Gln Asp Tyr Asp Trp His Val Phe Ser Leu Val Thr Thr Ile
                165                 170                 175

Phe Pro Gly Tyr Arg Asp Phe Ile Ser Phe Ile Lys Thr Thr Val Asp
            180                 185                 190

Asn Ser Phe Val Gly Trp Asp Met Gln Asn Val Ile Thr Leu Asp Thr
        195                 200                 205

Ser Phe Glu Asp Ala Lys Thr Gln Val Gln Leu Lys Lys Ile His Ser
210                 215                 220

Ser Val Ile Leu Leu Tyr Cys Ser Lys Asp Glu Ala Val Leu Ile Leu
225                 230                 235                 240

Ser Glu Ala Arg Ser Leu Gly Leu Thr Gly Tyr Asp Phe Phe Trp Ile
                245                 250                 255

Val Pro Ser Leu Val Ser Gly Asn Thr Glu Leu Ile Pro Lys Glu Phe
            260                 265                 270

Pro Ser Gly Leu Ile Ser Val Ser Tyr Asp Asp Trp Asp Tyr Ser Leu
        275                 280                 285

Glu Ala Arg Val Arg Asp Gly Leu Gly Ile Leu Thr Thr Ala Ala Ser
290                 295                 300

Ser Met Leu Glu Lys Phe Ser Tyr Ile Pro Glu Ala Lys Ala Ser Cys
305                 310                 315                 320

Tyr Gly Gln Ala Glu Lys Pro Glu Thr Pro Leu His Thr Leu His Gln
                325                 330                 335

Phe Met Val Asn Val Thr Trp Asp Gly Lys Asp Leu Ser Phe Thr Glu
            340                 345                 350

Glu Gly Tyr Gln Val His Pro Arg Leu Val Val Ile Val Leu Asn Lys
        355                 360                 365

Asp Arg Glu Trp Glu Lys Val Gly Lys Trp Glu Asn Gln Thr Leu Ser
370                 375                 380

Leu Arg His Ala Val Trp Pro Arg Tyr Lys Ser Phe Ser Asp Cys Glu
385                 390                 395                 400

Pro Asp Asp Asn His Leu Ser Ile Val Thr Leu Glu Glu Ala Pro Phe
                405                 410                 415

Val Ile Val Glu Asp Ile Asp Pro Leu Thr Glu Thr Cys Val Arg Asn
            420                 425                 430

Thr Val Pro Cys Arg Lys Phe Val Lys Ile Asn Asn Ser Thr Asn Glu
        435                 440                 445

Gly Met Asn Val Lys Lys Cys Cys Lys Gly Phe Cys Ile Asp Ile Leu
450                 455                 460

Lys Lys Leu Ser Arg Thr Val Lys Phe Thr Tyr Asp Leu Tyr Leu Val
465                 470                 475                 480

Thr Asn Gly Lys His Gly Lys Lys Val Asn Asn Val Trp Asn Gly Met
                485                 490                 495

Ile Gly Glu Val Val Tyr Gln Arg Ala Val Met Ala Val Gly Ser Leu
            500                 505                 510

Thr Ile Asn Glu Glu Arg Ser Glu Val Val Asp Phe Ser Val Pro Phe
        515                 520                 525

Val Glu Thr Gly Ile Ser Val Met Val Ser Arg Ser Asn Gly Thr Val
530                 535                 540

Ser Pro Ser Ala Phe Leu Glu Pro Phe Ser Ala Ser Val Trp Val Met
545                 550                 555                 560

Met Phe Val Met Leu Leu Ile Val Ser Ala Ile Ala Val Phe Val Phe
                565                 570                 575

Glu Tyr Phe Ser Pro Val Gly Tyr Asn Arg Asn Leu Ala Lys Gly Lys
```

-continued

```
                580                 585                 590
Ala Pro His Gly Pro Ser Phe Thr Ile Gly Lys Ala Ile Trp Leu Leu
            595                 600                 605

Trp Gly Leu Val Phe Asn Asn Ser Val Pro Val Gln Asn Pro Lys Gly
            610                 615                 620

Thr Thr Ser Lys Ile Met Val Ser Val Trp Ala Phe Phe Ala Val Ile
625                 630                 635                 640

Phe Leu Ala Ser Tyr Thr Ala Asn Leu Ala Ala Phe Met Ile Gln Glu
                    645                 650                 655

Glu Phe Val Asp Gln Val Thr Gly Leu Ser Asp Lys Lys Phe Gln Arg
            660                 665                 670

Pro His Asp Tyr Ser Pro Pro Phe Arg Phe Gly Thr Val Pro Asn Gly
            675                 680                 685

Ser Thr Glu Arg Asn Ile Arg Asn Asn Tyr Pro Tyr Met His Gln Tyr
            690                 695                 700

Met Thr Arg Phe Asn Gln Arg Gly Val Glu Asp Ala Leu Val Ser Leu
705                 710                 715                 720

Lys Thr Gly Lys Leu Asp Ala Phe Ile Tyr Asp Ala Ala Val Leu Asn
                    725                 730                 735

Tyr Lys Ala Gly Arg Asp Glu Gly Cys Lys Leu Val Thr Ile Gly Ser
            740                 745                 750

Gly Tyr Ile Phe Ala Ser Thr Gly Tyr Gly Ile Ala Leu Gln Lys Gly
            755                 760                 765

Ser Pro Trp Lys Arg Gln Ile Asp Leu Ala Leu Leu Gln Phe Val Gly
            770                 775                 780

Asp Gly Glu Met Glu Glu Leu Glu Thr Leu Trp Leu Thr Gly Ile Cys
785                 790                 795                 800

His Asn Glu Lys Asn Glu Val Met Ser Ser Gln Leu Asp Ile Asp Asn
                    805                 810                 815

Met Ala Gly Val Phe Tyr Met Leu Ala Ala Met Ala Leu Ser Leu
            820                 825                 830

Ile Thr Phe Ile Trp Glu His Leu Phe Tyr Trp Lys Leu Arg Phe Cys
            835                 840                 845

Phe Thr Gly Val Cys Ser Asp Arg Pro Gly Leu Leu Phe Ser Ile Ser
850                 855                 860

Arg Gly Ile Tyr Ser Cys Ile His Gly Val His Ile Glu Glu Lys Lys
865                 870                 875                 880

Lys Ser Pro Asp Phe Asn Leu Thr Gly Ser Gln Ser Asn Met Leu Lys
                    885                 890                 895

Leu Leu Arg Ser Ala Lys Asn Ile Ser Asn Met Ser Asn Met Asn Ser
            900                 905                 910

Ser Arg Met Asp Ser Pro Lys Arg Ala Thr Asp Phe Ile Gln Arg Gly
            915                 920                 925

Ser Leu Ile Val Asp Met Val Ser Asp Lys Gly Asn Leu Ile Tyr Ser
            930                 935                 940

Asp Asn Arg Ser Phe Gln Gly Lys Asp Ser Ile Phe Gly Asp Asn Met
945                 950                 955                 960

Asn Glu Leu Gln Thr Phe Val Ala Asn Arg His Lys Asp Asn Leu Ser
                    965                 970                 975

Asn Tyr Val Phe Gln Gly Gln His Pro Leu Thr Leu Asn Glu Ser Asn
            980                 985                 990

Pro Asn Thr Val Glu Val Ala Val  Ser Thr Glu Ser Lys  Gly Asn Ser
            995                      1000                   1005
```

-continued

```
Arg Pro Arg Gln Leu Trp Lys Lys Ser Met Glu Ser Leu Arg Gln
    1010                1015                1020

Asp Ser Leu Asn Gln Asn Pro Val Ser Gln Arg Asp Glu Lys Thr
    1025                1030                1035

Ala Glu Asn Arg Thr His Ser Leu Lys Ser Pro Arg Tyr Leu Pro
    1040                1045                1050

Glu Glu Val Ala His Ser Asp Ile Ser Glu Thr Ser Ser Arg Ala
    1055                1060                1065

Thr Cys His Arg Glu Pro Asp Asn Asn Lys Asn His Lys Thr Lys
    1070                1075                1080

Asp Asn Phe Lys Arg Ser Met Ala Ser Lys Tyr Pro Lys Asp Cys
    1085                1090                1095

Ser Asp Val Asp Arg Thr Tyr Met Lys Thr Lys Ala Ser Ser Pro
    1100                1105                1110

Arg Asp Lys Ile Tyr Thr Ile Asp Gly Glu Lys Glu Pro Ser Phe
    1115                1120                1125

His Leu Asp Pro Pro Gln Phe Val Glu Asn Ile Thr Leu Pro Glu
    1130                1135                1140

Asn Val Gly Phe Pro Asp Thr Tyr Gln Asp His Asn Glu Asn Phe
    1145                1150                1155

Arg Lys Gly Asp Ser Thr Leu Pro Met Asn Arg Asn Pro Leu His
    1160                1165                1170

Asn Glu Asp Gly Leu Pro Asn Asn Asp Gln Tyr Lys Leu Tyr Ala
    1175                1180                1185

Lys His Phe Thr Leu Lys Asp Lys Gly Ser Pro His Ser Glu Gly
    1190                1195                1200

Ser Asp Arg Tyr Arg Gln Asn Ser Thr His Cys Arg Ser Cys Leu
    1205                1210                1215

Ser Asn Leu Pro Thr Tyr Ser Gly His Phe Thr Met Arg Ser Pro
    1220                1225                1230

Phe Lys Cys Asp Ala Cys Leu Arg Met Gly Asn Leu Tyr Asp Ile
    1235                1240                1245

Asp Glu Asp Gln Met Leu Gln Glu Thr Gly Asn Pro Ala Thr Arg
    1250                1255                1260

Glu Glu Val Tyr Gln Gln Asp Trp Ser Gln Asn Asn Ala Leu Gln
    1265                1270                1275

Phe Gln Lys Asn Lys Leu Arg Ile Asn Arg Gln His Ser Tyr Asp
    1280                1285                1290

Asn Ile Leu Asp Lys Pro Arg Glu Ile Asp Leu Ser Arg Pro Ser
    1295                1300                1305

Arg Ser Ile Ser Leu Lys Asp Arg Glu Arg Leu Leu Glu Gly Asn
    1310                1315                1320

Leu Tyr Gly Ser Leu Phe Ser Val Pro Ser Ser Lys Leu Leu Gly
    1325                1330                1335

Asn Lys Ser Ser Leu Phe Pro Gln Gly Leu Glu Asp Ser Lys Arg
    1340                1345                1350

Ser Lys Ser Leu Leu Pro Asp His Ala Ser Asp Asn Pro Phe Leu
    1355                1360                1365

His Thr Tyr Gly Asp Asp Gln Arg Leu Val Ile Gly Arg Cys Pro
    1370                1375                1380

Ser Asp Pro Tyr Lys His Ser Leu Pro Ser Gln Ala Val Asn Asp
    1385                1390                1395
```

```
Ser Tyr Leu Arg Ser Ser Leu Arg Ser Thr Ala Ser Tyr Cys Ser
    1400                1405                1410

Arg Asp Ser Arg Gly His Ser Asp Val Tyr Ile Ser Glu His Val
    1415                1420                1425

Met Pro Tyr Ala Ala Asn Lys Asn Thr Met Tyr Ser Thr Pro Arg
    1430                1435                1440

Val Leu Asn Ser Cys Ser Asn Arg Arg Val Tyr Lys Lys Met Pro
    1445                1450                1455

Ser Ile Glu Ser Asp Val
    1460

<210> SEQ ID NO 2
<211> LENGTH: 536
<212> TYPE: PRT
<213> ORGANISM: homo sapiens

<400> SEQUENCE: 2

Pro Ala Gln Asn Ala Ala Glu Lys Gly Pro Ala Leu Asn Ile
1               5                   10                  15

Ala Val Leu Leu Gly His Ser His Asp Val Thr Glu Arg Glu Leu Arg
            20                  25                  30

Asn Leu Trp Gly Pro Glu Gln Ala Thr Gly Leu Pro Leu Asp Val Asn
        35                  40                  45

Val Val Ala Leu Leu Met Asn Arg Thr Asp Pro Lys Ser Leu Ile Thr
    50                  55                  60

His Val Cys Asp Leu Met Ser Gly Ala Arg Ile His Gly Leu Val Phe
65                  70                  75                  80

Gly Asp Asp Thr Asp Gln Glu Ala Val Ala Gln Met Leu Asp Phe Ile
                85                  90                  95

Ser Ser Gln Thr Phe Ile Pro Ile Leu Gly Ile His Gly Gly Ala Ser
            100                 105                 110

Met Ile Met Ala Asp Lys Asp Pro Thr Ser Thr Phe Phe Gln Phe Gly
        115                 120                 125

Ala Ser Ile Gln Gln Gln Ala Thr Val Met Leu Lys Ile Met Gln Asp
    130                 135                 140

Tyr Asp Trp His Val Phe Ser Leu Val Thr Thr Ile Phe Pro Gly Tyr
145                 150                 155                 160

Arg Asp Phe Ile Ser Phe Ile Lys Thr Thr Val Asp Asn Ser Phe Val
                165                 170                 175

Gly Trp Asp Met Gln Asn Val Ile Thr Leu Asp Thr Ser Phe Glu Asp
            180                 185                 190

Ala Lys Thr Gln Val Gln Leu Lys Lys Ile His Ser Ser Val Ile Leu
        195                 200                 205

Leu Tyr Cys Ser Lys Asp Glu Ala Val Leu Ile Leu Ser Glu Ala Arg
    210                 215                 220

Ser Leu Gly Leu Thr Gly Tyr Asp Phe Phe Trp Ile Val Pro Ser Leu
225                 230                 235                 240

Val Ser Gly Asn Thr Glu Leu Ile Pro Lys Glu Phe Pro Ser Gly Leu
                245                 250                 255

Ile Ser Val Ser Tyr Asp Asp Trp Asp Tyr Ser Leu Glu Ala Arg Val
            260                 265                 270

Arg Asp Gly Leu Gly Ile Leu Thr Thr Ala Ala Ser Ser Met Leu Glu
        275                 280                 285

Lys Phe Ser Tyr Ile Pro Glu Ala Lys Ala Ser Cys Tyr Gly Gln Ala
    290                 295                 300
```

```
Glu Lys Pro Glu Thr Pro Leu His Thr Leu His Gln Phe Met Val Asn
305                 310                 315                 320

Val Thr Trp Asp Gly Lys Asp Leu Ser Phe Thr Glu Glu Gly Tyr Gln
            325                 330                 335

Val His Pro Arg Leu Val Ile Val Leu Asn Lys Asp Arg Glu Trp
        340                 345                 350

Glu Lys Val Gly Lys Trp Glu Asn Gln Thr Leu Ser Leu Arg His Ala
            355                 360                 365

Val Trp Pro Arg Tyr Lys Ser Phe Ser Asp Cys Glu Pro Asp Asp Asn
        370                 375                 380

His Leu Ser Ile Val Thr Leu Glu Glu Ala Pro Phe Val Ile Val Glu
385                 390                 395                 400

Asp Ile Asp Pro Leu Thr Glu Thr Cys Val Arg Asn Thr Val Pro Cys
                405                 410                 415

Arg Lys Phe Val Lys Ile Asn Asn Ser Thr Asn Glu Gly Met Asn Val
            420                 425                 430

Lys Lys Cys Cys Lys Gly Phe Cys Ile Asp Ile Leu Lys Lys Leu Ser
        435                 440                 445

Arg Thr Val Lys Phe Thr Tyr Asp Leu Tyr Leu Val Thr Asn Gly Lys
    450                 455                 460

His Gly Lys Lys Val Asn Asn Val Trp Asn Gly Met Ile Gly Glu Val
465                 470                 475                 480

Val Tyr Gln Arg Ala Val Met Ala Val Gly Ser Leu Thr Ile Asn Glu
                485                 490                 495

Glu Arg Ser Glu Val Val Asp Phe Ser Val Pro Phe Val Glu Thr Gly
            500                 505                 510

Ile Ser Val Met Val Ser Arg Ser Asn Gly Thr Val Ser Pro Ser Ala
        515                 520                 525

Phe Leu Glu Pro Phe Ser Ala Ser
    530                 535

<210> SEQ ID NO 3
<211> LENGTH: 21
<212> TYPE: PRT
<213> ORGANISM: homo sapiens

<400> SEQUENCE: 3

Asn Gly Met Ile Gly Glu Val Val Tyr Gln Arg Ala Val Met Ala Val
1               5                   10                  15

Gly Ser Leu Thr Ile
            20

<210> SEQ ID NO 4
<211> LENGTH: 22
<212> TYPE: PRT
<213> ORGANISM: artificial sequence
<220> FEATURE:
<223> OTHER INFORMATION: modified amino acid sequence

<400> SEQUENCE: 4

Cys Asn Gly Met Ile Gly Glu Val Val Tyr Gln Arg Ala Val Met Ala
1               5                   10                  15

Val Gly Ser Leu Thr Ile
            20

<210> SEQ ID NO 5
<211> LENGTH: 6293
```

<212> TYPE: DNA
<213> ORGANISM: homo sapiens

<400> SEQUENCE: 5

| | | | | | |
|---|---|---|---|---|---|
| atcatgggac | cgggtgagcg | ctgagaatcg | cggccgcagc | catcagccct | ggagatgacc | 60 |
| aggagcggcc | actgctgaga | actatgtgga | gagaggctgc | gagccctgct | gcagagcctc | 120 |
| cggctgggat | agccgccccc | cgtggggcg | atgcggacag | cgcggacag | ccaggggagc | 180 |
| gcgctgggc | cgcagcatgc | gggaacccgc | taaacccggt | ggctgctgag | gcggccgaga | 240 |
| tgctcgtgcg | cgcagcgcgc | cccactgcat | cctcgacctt | ctcgggctac | agggaccgtc | 300 |
| agtggcgact | atgggcagag | tgggctattg | gaccctgctg | gtgctgccgg | cccttctggt | 360 |
| ctggcgcggt | ccgcgccga | gcgcggcggc | ggagaagggt | cccccgcgc | taaatattgc | 420 |
| ggtgatgctg | ggtcacagcc | acgacgtgac | agagcgcgaa | cttcgaacac | tgtggggccc | 480 |
| cgagcaggcg | gcggggctgc | ccctggacgt | gaacgtggta | gctctgctga | tgaaccgcac | 540 |
| cgaccccaag | agcctcatca | cgcacgtgtg | cgacctcatg | tccggggcac | gcatccacgg | 600 |
| cctcgtgttt | ggggacgaca | cggaccagga | ggccgtagcc | cagatgctgg | attttatctc | 660 |
| ctcccacacc | ttcgtcccca | tcttgggcat | tcatgggggc | gcatctatga | tcatggctga | 720 |
| caaggatccg | acgtctacct | tcttccagtt | tggagcgtcc | atccagcagc | aagccacggt | 780 |
| catgctgaag | atcatgcagg | attatgactg | gcatgtcttc | tccctggtga | ccactatctt | 840 |
| ccctggctac | agggaattca | tcagcttcgt | caagaccaca | gtggacaaca | gctttgtggg | 900 |
| ctgggacatg | cagaatgtga | tcacactgga | cacttccttt | gaggatgcaa | agacacaagt | 960 |
| ccagctgaag | aagatccact | cttctgtcat | cttgctctac | tgttccaaag | acgaggctgt | 1020 |
| tctcattctg | agtgaggccc | gctcccttgg | cctcaccggg | tatgatttct | ctggattgt | 1080 |
| ccccagcttg | gtctctggga | acacggagct | catcccaaaa | gagtttccat | cgggactcat | 1140 |
| ttctgtctcc | tacgatgact | gggactacag | cctggaggcg | agagtgaggg | acggcattgg | 1200 |
| catcctaacc | accgctgcat | cttctatgct | ggagaagttc | tcctacatcc | ccgaggccaa | 1260 |
| ggccagctgc | tacgggcaga | tggagaggcc | agaggtcccg | atgcacacct | tgcacccatt | 1320 |
| tatggtcaat | gttacatggg | atggcaaaga | cttatccttc | actgaggaag | gctaccaggt | 1380 |
| gcaccccagg | ctggtggtga | ttgtgctgaa | caaagaccgg | gaatgggaaa | aggtgggcaa | 1440 |
| gtgggagaac | catacgctga | gcctgaggca | cgccgtgtgg | cccaggtaca | agtccttctc | 1500 |
| cgactgtgag | ccggatgaca | accatctcag | catcgtcacc | ctggaggagg | ccccattcgt | 1560 |
| catcgtggaa | gacatagacc | ccctgaccga | gacgtgtgtg | aggaacaccg | tgccatgtcg | 1620 |
| gaagttcgtc | aaaatcaaca | attcaaccaa | tgagggatg | aatgtgaaga | aatgctgcaa | 1680 |
| ggggttctgc | attgatattc | tgaagaagct | ttccagaact | gtgaagttta | cttacgacct | 1740 |
| ctatctggtg | accaatggga | agcatggcaa | gaaagttaac | aatgtgtgga | atggaatgat | 1800 |
| cggtgaagtg | gtctatcaac | gggcagtcat | ggcagttggc | tcgctcacca | tcaatgagga | 1860 |
| acgttctgaa | gtggtggact | ctctctgtgcc | ctttgtggaa | acgggaatca | gtgtcatggt | 1920 |
| ttcaagaagt | aatggcaccg | tctcacccttc | tgcttttcta | gaaccattca | gcgcctctgt | 1980 |
| ctgggtgatg | atgtttgtga | tgctgctcat | tgtttctgcc | atagctgttt | ttgtctttga | 2040 |
| atacttcagc | cctgttggat | acaacagaaa | cttagccaaa | gggaaagcac | ccatgggcc | 2100 |
| ttcttttaca | attggaaaag | ctatatggct | tcttttgggc | ctggtgttca | ataactccgt | 2160 |
| gcctgtccag | aatcctaaag | ggaccaccag | caagatcatg | gtatctgtat | gggccttctt | 2220 |

```
cgctgtcata ttcctggcta gctacacagc caatctggct gccttcatga tccaagagga   2280
atttgtggac caagtgaccg gcctcagtga caaaaagttt cagagacctc atgactattc   2340
cccacctttt cgatttggga cagtgcctaa tggaagcacg gagagaaaca ttcggaataa   2400
ctatccctac atgcatcagt acatgaccaa atttaatcag aaaggagtag aggacgcctt   2460
ggtcagcctg aaaacgggga agctggacgc tttcatctac gatgccgcag tcttgaatta   2520
caaggctggg agggatgaag gctgcaagct ggtgaccatc gggagtgggt acatctttgc   2580
caccaccggt tatggaattg cccttcagaa aggctctcct tggaagaggc agatcgacct   2640
ggccttgctt cagtttgtgg gtgatggtga gatggaggag ctggagaccc tgtggctcac   2700
tgggatctgc cacaacgaga gaacgaggt gatgagcagc cagctggaca ttgacaacat   2760
ggcgggcgta ttctacatgc tggctgccgc catggccctt agcctcatca ccttcatctg   2820
ggagcacctc ttctactgga agctgcgctt ctgtttcacg ggcgtgtgct ccgaccggcc   2880
tgggttgctc ttctccatca gcaggggcat ctacagctgc attcatggag tgcacattga   2940
agaaaagaag aagtctccag acttcaatct gacgggatcc cagagcaaca tgttaaaact   3000
cctccggtca gccaaaaaca tttcagcat gtccaacatg aactcctcaa gaatggactc   3060
acccaaaaga gctgctgact tcatccaaag aggttccctc atcatggaca tggtttcaga   3120
taaggggaat tgatgtact cagacaacag gtccttcag gggaagaga gcattttgg    3180 agacaacatg aacgaactcc aaacatttgt ggccaaccgg cagaaggata acctcaataa   3240
ctatgtattc cagggacaac atcctcttac tctcaatgag tccaacccta cacggtgga   3300 ggtggccgtg agcacagaat ccaaagcgaa ctctagaccc cggcagctgt ggaagaaatc   3360
cgtggattcc atacgccagg attcactatc ccagaatcca gtctcccaga gggatgaggc   3420
aacagcagag aataggaccc actccctaaa gagccctagg tatcttccag aagagatggc   3480
ccactctgac atttcagaaa cgtcaaatcg ggccacgtgc cacagggaac ctgacaacag   3540
taagaaccac aaaaccaagg acaactttaa aaggtcagtg gcctccaaat ccccaagga   3600 ctgtagtgag gtcgagcgca cctacctgaa aaccaaatca agctccccta gagacaagat   3660
ctacactata gatggtgaga aggagcctgg tttccactta gatccacccc agtttgttga   3720
aaatgtgacc ctgcccgaga cgtggactt cccggacccc taccaggatc ccagtgaaaa   3780
cttccgcaag ggggactcca cgctgccaat gaaccggaac cccttgcata tgaagagggg   3840
gctttccaac aacgaccagt ataaactcta ctccaagcac ttcaccttga agacaagggg   3900
ttccccgcac agtgagacca cgagcgata ccggcagaac tccacgcact gcagaagctg   3960
cctttccaac atgcccacct attcaggcca cttcaccatg aggtcccct tcaagtgcga   4020 tgcctgcctg cggatgggga acctctatga catcgatgaa gaccagatgc ttcaggagac   4080
aggtaaccca gccaccgggg agcaggtcta ccagcaggac tgggcacaga acaatgccct   4140
tcaattacaa aagaacaagc taaggattag ccgtcagcat tcctacgata acattgtcga   4200
caaacctagg gagctagacc ttagcaggcc ctccggagc ataagcctca aggacaggga   4260
acggcttctg gagggaaatt tttacggcag cctgtttagt gtcccctcaa gcaaactctc   4320
ggggaaaaaa agctccctt tccccccaagg tctggaggac agcaagagga gcaagtctct   4380
cttgccagac cacacctccg ataacccttt cctccactcc cacagggatg accaacgctt   4440
ggttattggg agatgcccct cggacccta caaacactcg ttgccatccc aggcggtgaa   4500
tgacagctat cttcggtcgt ccttgaggtc aacggcatcg tactgttcca gggacagtcg   4560
gggccacaat gatgtgtata tttcggagca tgttatgcct tatgctgcaa ataagaataa   4620
```

```
tatgtactct accccaggg ttttaaattc ctgcagcaat agacgcgtgt acaagaaaat    4680
gcctagtatc gaatctgatg tttaaaaatc ttccattaat gttttatcta tagggaaata    4740
cacgtaatgg ccaatgttct ggagggtaaa tgttggatgt ccaatagtgc cctgctaaga    4800
ggaagaagat gtagggaggt attttgttgt tgttgttgtt ggctcttttg cacacggctt    4860
catgccataa tcttccactc aaggaatctt gtgaggtgtg tgctgagcat ggcagacacc    4920
agataggtga gtccttaacc aaaaataact aactacataa gggcaagtct ccgggacatg    4980
cctactgggt atgttggcaa taatgatgca ttggatgcca atggtgatgt tatgatttcc    5040
tatattccaa attccattaa ggtcagccca ccatgtaatt ttctcatcag aaatgcctaa    5100
tggtttctct aatacagaat aagcaatatg gtgtgcatgt aaacctgaca cagacaaaat    5160
aaaaacagtt aagaatgcat ctgcactgta gtcggatttg aacatgtgca agagattagg    5220
aagtttggct cgtaacagtt tcagctttct tgttatgcct tccatcacag cccaggctca    5280
ccccaagaac tccaggctcc cctaaagaat agcaaatcag tgtgttcgtg atgactgtgc    5340
taccttcatt atagttcatt ccaagacac atctggagcc aaaggcccga gggaccctca     5400
ggtggggaga gctacaggaa tctctttgga tgttgatgtg tgtttctctc taccctcggc    5460
ttcgatggtc ttgttcagag ctgcataaac taacacattt atgtctccga gatctaagtg    5520
tggatcttct gtctgtgaca cagtggccat tgtagtttat cccgaagacg cctatgtacg    5580
taagtttgca tttcctccct tctggtgatg actcagggtt gtatagtatc tgttacccct    5640
tccctcccag agtaaccata actcgttccg tttccaaaca gccatggtgg tgtccaatta    5700
gctgtgtatc gctcttccca gagttgttaa tgtggtgaca tgcaccaaca gccgtatgtg    5760
tactgtgatc tgtaagaagt acaatgccat ctgtctgccg aaggctagca tggttttagg    5820
tttatcttcc ttcacatcca gaaattctgt tggacactca cttccacccc aaactcctca    5880
aatcaaaagc cttcaaaaca cgaggcactc ttggatctac cctgagtatc ctccaaactg    5940
tggatacagt ttagtgagac aagcaatttc tcccttctga gttattctct ctgttggtgg    6000
caaaccactt catagcacca acagagatgt aggaaaaatt cctcaaagta tttgtcattt    6060
ctgagtcgcc tgcattatcc cattcttatt ctcctcaaac ctgtgcatat atgacatgaa    6120
atgatatcca tttttttttt aagttagaaa cagagagggg aatacttatg catggggagc    6180
ctgttagcac agtgcctgcc acaaaaacaa gtgcccccga caagatagtt gctatgttat    6240
gacactttct cagatcagga ttttctagtt taaaaattaa atatcataaa acg           6293
```

<210> SEQ ID NO 6
<211> LENGTH: 1608
<212> TYPE: DNA
<213> ORGANISM: homo sapiens

<400> SEQUENCE: 6

```
ccggcgccga gcgcggcggc ggagaagggt cccccgcgc taaatattgc ggtgatgctg      60
ggtcacagcc acgacgtgac agagcgcgaa cttcgaacac tgtggggccc cgagcaggcg    120
gcggggctgc ccctggacgt gaacgtggta gctctgctga tgaaccgcac cgaccccaag    180
agcctcatca cgcacgtgtg cgacctcatg tccggggcac gcatccacgg cctcgtgttt    240
ggggacgaca cggaccagga ggccgtagcc cagatgctgg attttatctc ctcccacacc    300
ttcgtcccca tctgggcat tcatggggc gcatctatga tcatggctga caaggatccg    360
acgtctacct tcttccagtt tggagcgtcc atccagcagc aagccacggt catgctgaag    420
```

-continued

| | |
|---|---|
| atcatgcagg attatgactg gcatgtcttc tccctggtga ccactatctt ccctggctac | 480 |
| agggaattca tcagcttcgt caagaccaca gtggacaaca gctttgtggg ctgggacatg | 540 |
| cagaatgtga tcacactgga cacttccttt gaggatgcaa agacacaagt ccagctgaag | 600 |
| aagatccact cttctgtcat cttgctctac tgttccaaag acgaggctgt tctcattctg | 660 |
| agtgaggccc gctcccttgg cctcaccggg tatgatttct tctggattgt ccccagcttg | 720 |
| gtctctggga acacggagct catcccaaaa gagtttccat cgggactcat ttctgtctcc | 780 |
| tacgatgact gggactacag cctggaggcg agagtgaggg acggcattgg catcctaacc | 840 |
| accgctgcat cttctatgct ggagaagttc tcctacatcc ccgaggccaa ggccagctgc | 900 |
| tacgggcaga tggagaggcc agaggtcccg atgcacacct tgcacccatt tatggtcaat | 960 |
| gttacatggg atggcaaaga cttatccttc actgaggaag ctaccaggt gcaccccagg | 1020 |
| ctggtggtga ttgtgctgaa caaagaccgg gaatgggaaa aggtgggcaa gtgggagaac | 1080 |
| catacgctga gcctgaggca cgccgtgtgg cccaggtaca agtccttctc cgactgtgag | 1140 |
| ccggatgaca accatctcag catcgtcacc ctggaggagg ccccattcgt catcgtggaa | 1200 |
| gacatagacc ccctgaccga gacgtgtgtg aggaacaccg tgccatgtcg gaagttcgtc | 1260 |
| aaaatcaaca attcaaccaa tgaggggatg aatgtgaaga aatgctgcaa ggggttctgc | 1320 |
| attgatattc tgaagaagct ttccagaact gtgaagtttta cttacgacct ctatctggtg | 1380 |
| accaatggga agcatggcaa gaaagttaac aatgtgtgga atggaatgat cggtgaagtg | 1440 |
| gtctatcaac gggcagtcat ggcagttggc tcgctcacca tcaatgagga acgttctgaa | 1500 |
| gtggtggact ctctctgtgcc ctttgtggaa acgggaatca gtgtcatggt ttcaagaagt | 1560 |
| aatggcaccg tctcaccttc tgcttttcta gaaccattca gcgcctct | 1608 |

<210> SEQ ID NO 7
<211> LENGTH: 62
<212> TYPE: DNA
<213> ORGANISM: homo sapiens

<400> SEQUENCE: 7

| | |
|---|---|
| atggaatgat cggtgaagtg gtctatcaac gggcagtcat ggcagttggc tcgctcacca | 60 |
| tc | 62 |

<210> SEQ ID NO 8
<211> LENGTH: 21
<212> TYPE: DNA
<213> ORGANISM: artificial sequence
<220> FEATURE:
<223> OTHER INFORMATION: oligonucleotide primer

<400> SEQUENCE: 8

| | |
|---|---|
| agcatggcaa gaaagttaac a | 21 |

<210> SEQ ID NO 9
<211> LENGTH: 21
<212> TYPE: DNA
<213> ORGANISM: artificial sequence
<220> FEATURE:
<223> OTHER INFORMATION: oligonucleotide primer

<400> SEQUENCE: 9

| | |
|---|---|
| acgttctgaa gtggtggact t | 21 |

<210> SEQ ID NO 10
<211> LENGTH: 1480

```
<212> TYPE: PRT
<213> ORGANISM: homo sapiens

<400> SEQUENCE: 10

Met Lys Pro Arg Ala Glu Cys Cys Ser Pro Lys Phe Trp Leu Val Leu
1               5                   10                  15

Ala Val Leu Ala Val Ser Gly Ser Arg Ala Arg Ser Gln Lys Ser Pro
            20                  25                  30

Pro Ser Ile Gly Ile Ala Val Ile Leu Val Gly Thr Ser Asp Glu Val
        35                  40                  45

Ala Ile Lys Asp Ala His Glu Lys Asp Phe His His Leu Ser Val
50                  55                  60

Val Pro Arg Val Glu Leu Val Ala Met Asn Glu Thr Asp Pro Lys Ser
65                  70                  75                  80

Ile Ile Thr Arg Ile Cys Asp Leu Met Ser Asp Arg Lys Ile Gln Gly
                85                  90                  95

Val Val Phe Ala Asp Asp Thr Asp Gln Glu Ala Ile Ala Gln Ile Leu
            100                 105                 110

Asp Phe Ile Ser Ala Gln Thr Leu Thr Pro Ile Leu Gly Ile His Gly
        115                 120                 125

Gly Ser Ser Met Ile Met Ala Asp Lys Asp Glu Ser Ser Met Phe Phe
130                 135                 140

Gln Phe Gly Pro Ser Ile Glu Gln Gln Ala Ser Val Met Leu Asn Ile
145                 150                 155                 160

Met Glu Glu Tyr Asp Trp Tyr Ile Phe Ser Ile Val Thr Thr Tyr Phe
                165                 170                 175

Pro Gly Tyr Gln Asp Phe Val Asn Lys Ile Arg Ser Thr Ile Glu Asn
            180                 185                 190

Ser Phe Val Gly Trp Glu Leu Glu Glu Val Leu Leu Leu Asp Met Ser
        195                 200                 205

Leu Asp Asp Gly Asp Ser Lys Ile Gln Asn Gln Leu Lys Lys Leu Gln
210                 215                 220

Ser Pro Ile Ile Leu Leu Tyr Cys Thr Lys Glu Glu Ala Thr Tyr Ile
225                 230                 235                 240

Phe Glu Val Ala Asn Ser Val Gly Leu Thr Gly Tyr Gly Tyr Thr Trp
                245                 250                 255

Ile Val Pro Ser Leu Val Ala Gly Asp Thr Asp Thr Val Pro Ala Glu
            260                 265                 270

Phe Pro Thr Gly Leu Ile Ser Val Ser Tyr Asp Glu Trp Asp Tyr Gly
        275                 280                 285

Leu Pro Ala Arg Val Arg Asp Gly Ile Ala Ile Thr Thr Ala Ala
290                 295                 300

Ser Asp Met Leu Ser Glu His Ser Phe Ile Pro Glu Pro Lys Ser Ser
305                 310                 315                 320

Cys Tyr Asn Thr His Glu Lys Arg Ile Tyr Gln Ser Asn Met Leu Asn
                325                 330                 335

Arg Tyr Leu Ile Asn Val Thr Phe Glu Gly Arg Asn Leu Ser Phe Ser
            340                 345                 350

Glu Asp Gly Tyr Gln Met His Pro Lys Leu Val Ile Leu Leu Asn
        355                 360                 365

Lys Glu Arg Lys Trp Glu Arg Val Gly Lys Trp Lys Asp Lys Ser Leu
370                 375                 380

Gln Met Lys Tyr Tyr Val Trp Pro Arg Met Cys Pro Glu Thr Glu Glu
385                 390                 395                 400
```

```
Gln Glu Asp Asp His Leu Ser Ile Val Thr Leu Glu Glu Ala Pro Phe
            405                 410                 415
Val Ile Val Glu Ser Val Asp Pro Leu Ser Gly Thr Cys Met Arg Asn
        420                 425                 430
Thr Val Pro Cys Gln Lys Arg Ile Val Thr Glu Asn Lys Thr Asp Glu
    435                 440                 445
Glu Pro Gly Tyr Ile Lys Lys Cys Cys Lys Gly Phe Cys Ile Asp Ile
450                 455                 460
Leu Lys Lys Ile Ser Lys Ser Val Lys Phe Thr Tyr Asp Leu Tyr Leu
465                 470                 475                 480
Val Thr Asn Gly Lys His Gly Lys Lys Ile Asn Gly Thr Trp Asn Gly
            485                 490                 495
Met Ile Gly Glu Val Val Met Lys Arg Ala Tyr Met Ala Val Gly Ser
            500                 505                 510
Leu Thr Ile Asn Glu Glu Arg Ser Glu Val Val Asp Phe Ser Val Pro
        515                 520                 525
Phe Ile Glu Thr Gly Ile Ser Val Met Val Ser Arg Ser Asn Gly Thr
    530                 535                 540
Val Ser Pro Ser Ala Phe Leu Glu Pro Phe Ser Ala Asp Val Trp Val
545                 550                 555                 560
Met Met Phe Val Met Leu Leu Ile Val Ser Ala Val Ala Val Phe Val
            565                 570                 575
Phe Glu Tyr Phe Ser Pro Val Gly Tyr Asn Arg Cys Leu Ala Asp Gly
            580                 585                 590
Arg Glu Pro Gly Gly Pro Ser Phe Thr Ile Gly Lys Ala Ile Trp Leu
        595                 600                 605
Leu Trp Gly Leu Val Phe Asn Asn Ser Val Pro Val Gln Asn Pro Lys
    610                 615                 620
Gly Thr Thr Ser Lys Ile Met Val Ser Val Trp Ala Phe Phe Ala Val
625                 630                 635                 640
Ile Phe Leu Ala Ser Tyr Thr Ala Asn Leu Ala Ala Phe Met Ile Gln
            645                 650                 655
Glu Glu Tyr Val Asp Gln Val Ser Gly Leu Ser Asp Lys Lys Phe Gln
            660                 665                 670
Arg Pro Asn Asp Phe Ser Pro Pro Phe Arg Phe Gly Thr Val Pro Asn
        675                 680                 685
Gly Ser Thr Glu Arg Asn Ile Arg Asn Asn Tyr Ala Glu Met His Ala
    690                 695                 700
Tyr Met Gly Lys Phe Asn Gln Arg Gly Val Asp Asp Ala Leu Leu Ser
705                 710                 715                 720
Leu Lys Thr Gly Lys Leu Asp Ala Phe Ile Tyr Asp Ala Ala Val Leu
            725                 730                 735
Asn Tyr Met Ala Gly Arg Asp Glu Gly Cys Lys Leu Val Thr Ile Gly
            740                 745                 750
Ser Gly Lys Val Phe Ala Ser Thr Gly Tyr Gly Ile Ala Ile Gln Lys
        755                 760                 765
Asp Ser Gly Trp Lys Arg Gln Val Asp Leu Ala Ile Leu Gln Leu Phe
    770                 775                 780
Gly Asp Gly Glu Met Glu Glu Leu Glu Ala Leu Trp Leu Thr Gly Ile
785                 790                 795                 800
Cys His Asn Glu Lys Asn Glu Val Met Ser Ser Gln Leu Asp Ile Asp
            805                 810                 815
```

```
Asn Met Ala Gly Val Phe Tyr Met Leu Gly Ala Ala Met Ala Leu Ser
            820                 825                 830

Leu Ile Thr Phe Ile Cys Glu His Leu Phe Tyr Trp Gln Phe Arg His
            835                 840                 845

Cys Phe Met Gly Val Cys Ser Gly Lys Pro Gly Met Val Phe Ser Ile
850                 855                 860

Ser Arg Gly Ile Tyr Ser Cys Ile His Gly Val Ala Ile Glu Glu Arg
865                 870                 875                 880

Gln Ser Val Met Asn Ser Pro Thr Ala Thr Met Asn Asn Thr His Ser
                885                 890                 895

Asn Ile Leu Arg Leu Leu Arg Thr Ala Lys Asn Met Ala Asn Leu Ser
            900                 905                 910

Gly Val Asn Gly Ser Pro Gln Ser Ala Leu Asp Phe Ile Arg Arg Glu
            915                 920                 925

Ser Ser Val Tyr Asp Ile Ser Glu His Arg Arg Ser Phe Thr His Ser
930                 935                 940

Asp Cys Lys Ser Tyr Asn Asn Pro Pro Cys Glu Glu Asn Leu Phe Ser
945                 950                 955                 960

Asp Tyr Ile Ser Glu Val Glu Arg Thr Phe Gly Asn Leu Gln Leu Lys
                965                 970                 975

Asp Ser Asn Val Tyr Gln Asp His Tyr His His His Arg Pro His
            980                 985                 990

Ser Ile Gly Ser Ala Ser Ser Ile Asp Gly Leu Tyr Asp Cys Asp Asn
            995                 1000                1005

Pro Pro Phe Thr Thr Gln Ser Arg Ser Ile Ser Lys Lys Pro Leu
    1010                1015                1020

Asp Ile Gly Leu Pro Ser Ser Lys His Ser Gln Leu Ser Asp Leu
    1025                1030                1035

Tyr Gly Lys Phe Ser Phe Lys Ser Asp Arg Tyr Ser Gly His Asp
    1040                1045                1050

Asp Leu Ile Arg Ser Asp Val Ser Asp Ile Ser Thr His Thr Val
    1055                1060                1065

Thr Tyr Gly Asn Ile Glu Gly Asn Ala Ala Lys Arg Arg Lys Gln
    1070                1075                1080

Gln Tyr Lys Asp Ser Leu Lys Lys Arg Pro Ala Ser Ala Lys Ser
    1085                1090                1095

Arg Arg Glu Phe Asp Glu Ile Glu Leu Ala Tyr Arg Arg Arg Pro
    1100                1105                1110

Pro Arg Ser Pro Asp His Lys Arg Tyr Phe Arg Asp Lys Glu Gly
    1115                1120                1125

Leu Arg Asp Phe Tyr Leu Asp Gln Phe Arg Thr Lys Glu Asn Ser
    1130                1135                1140

Pro His Trp Glu His Val Asp Leu Thr Asp Ile Tyr Lys Glu Arg
    1145                1150                1155

Ser Asp Asp Phe Lys Arg Asp Ser Val Ser Gly Gly Pro Cys
    1160                1165                1170

Thr Asn Arg Ser His Ile Lys His Gly Thr Gly Asp Lys His Gly
    1175                1180                1185

Val Val Ser Gly Val Pro Ala Pro Trp Glu Lys Asn Leu Thr Asn
    1190                1195                1200

Val Glu Trp Glu Asp Arg Ser Gly Gly Asn Phe Cys Arg Ser Cys
    1205                1210                1215

Pro Ser Lys Leu His Asn Tyr Ser Thr Thr Val Thr Gly Gln Asn
```

```
                       1220                1225                1230

Ser Gly Arg Gln Ala Cys Ile Arg Cys Glu Ala Cys Lys Lys Ala
    1235                1240                1245

Gly Asn Leu Tyr Asp Ile Ser Glu Asp Asn Ser Leu Gln Glu Leu
    1250                1255                1260

Asp Gln Pro Ala Ala Pro Val Ala Val Thr Ser Asn Ala Ser Thr
    1265                1270                1275

Thr Lys Tyr Pro Gln Ser Pro Thr Asn Ser Lys Ala Gln Lys Lys
    1280                1285                1290

Asn Arg Asn Lys Leu Arg Arg Gln His Ser Tyr Asp Thr Phe Val
    1295                1300                1305

Asp Leu Gln Lys Glu Ala Ala Leu Ala Pro Arg Ser Val Ser
    1310                1315                1320

Leu Lys Asp Lys Gly Arg Phe Met Asp Gly Ser Pro Tyr Ala His
    1325                1330                1335

Met Phe Glu Met Ser Ala Gly Glu Ser Thr Phe Ala Asn Asn Lys
    1340                1345                1350

Ser Ser Val Pro Thr Ala Gly His His His Asn Asn Pro Gly
    1355                1360                1365

Gly Gly Tyr Met Leu Ser Lys Ser Leu Tyr Pro Asp Arg Val Thr
    1370                1375                1380

Gln Asn Pro Phe Ile Pro Thr Phe Gly Asp Asp Gln Cys Leu Leu
    1385                1390                1395

His Gly Ser Lys Ser Tyr Phe Phe Arg Gln Pro Thr Val Ala Gly
    1400                1405                1410

Ala Ser Lys Ala Arg Pro Asp Phe Arg Ala Leu Val Thr Asn Lys
    1415                1420                1425

Pro Val Val Ser Ala Leu His Gly Ala Val Pro Ala Arg Phe Gln
    1430                1435                1440

Lys Asp Ile Cys Ile Gly Asn Gln Ser Asn Pro Cys Val Pro Asn
    1445                1450                1455

Asn Lys Asn Pro Arg Ala Phe Asn Gly Ser Ser Asn Gly His Val
    1460                1465                1470

Tyr Glu Lys Leu Ser Ser Ile
    1475                1480

<210> SEQ ID NO 11
<211> LENGTH: 531
<212> TYPE: PRT
<213> ORGANISM: homo sapiens

<400> SEQUENCE: 11

Arg Ser Gln Lys Ser Pro Pro Ser Ile Gly Ile Ala Val Ile Leu Val
1               5                   10                  15

Gly Thr Ser Asp Glu Val Ala Ile Lys Asp Ala His Glu Lys Asp Asp
                20                  25                  30

Phe His His Leu Ser Val Val Pro Arg Val Glu Leu Val Ala Met Asn
            35                  40                  45

Glu Thr Asp Pro Lys Ser Ile Ile Thr Arg Ile Cys Asp Leu Met Ser
        50                  55                  60

Asp Arg Lys Ile Gln Gly Val Val Phe Ala Asp Asp Thr Asp Gln Glu
65                  70                  75                  80

Ala Ile Ala Gln Ile Leu Asp Phe Ile Ser Ala Gln Thr Leu Thr Pro
                85                  90                  95
```

```
Ile Leu Gly Ile His Gly Gly Ser Ser Met Ile Met Ala Asp Lys Asp
            100                 105                 110
Glu Ser Ser Met Phe Gln Phe Gly Pro Ser Ile Glu Gln Gln Ala
        115                 120                 125
Ser Val Met Leu Asn Ile Met Glu Glu Tyr Asp Trp Tyr Ile Phe Ser
    130                 135                 140
Ile Val Thr Thr Tyr Phe Pro Gly Tyr Gln Asp Phe Val Asn Lys Ile
145                 150                 155                 160
Arg Ser Thr Ile Glu Asn Ser Phe Val Gly Trp Glu Leu Glu Glu Val
                165                 170                 175
Leu Leu Leu Asp Met Ser Leu Asp Asp Gly Asp Ser Lys Ile Gln Asn
            180                 185                 190
Gln Leu Lys Lys Leu Gln Ser Pro Ile Ile Leu Leu Tyr Cys Thr Lys
        195                 200                 205
Glu Glu Ala Thr Tyr Ile Phe Glu Val Ala Asn Ser Val Gly Leu Thr
    210                 215                 220
Gly Tyr Gly Tyr Thr Trp Ile Val Pro Ser Leu Val Ala Gly Asp Thr
225                 230                 235                 240
Asp Thr Val Pro Ala Glu Phe Pro Thr Gly Leu Ile Ser Val Ser Tyr
                245                 250                 255
Asp Glu Trp Asp Tyr Gly Leu Pro Ala Arg Val Arg Asp Gly Ile Ala
            260                 265                 270
Ile Ile Thr Thr Ala Ala Ser Asp Met Leu Ser Glu His Ser Phe Ile
        275                 280                 285
Pro Glu Pro Lys Ser Ser Cys Tyr Asn Thr His Glu Lys Arg Ile Tyr
    290                 295                 300
Gln Ser Asn Met Leu Asn Arg Tyr Leu Ile Asn Val Thr Phe Glu Gly
305                 310                 315                 320
Arg Asn Leu Ser Phe Ser Glu Asp Gly Tyr Gln Met His Pro Lys Leu
                325                 330                 335
Val Ile Ile Leu Leu Asn Lys Glu Arg Lys Trp Glu Arg Val Gly Lys
            340                 345                 350
Trp Lys Asp Lys Ser Leu Gln Met Lys Tyr Tyr Val Trp Pro Arg Met
        355                 360                 365
Cys Pro Glu Thr Glu Glu Gln Glu Asp Asp His Leu Ser Ile Val Thr
    370                 375                 380
Leu Glu Glu Ala Pro Phe Val Ile Val Glu Ser Val Asp Pro Leu Ser
385                 390                 395                 400
Gly Thr Cys Met Arg Asn Thr Val Pro Cys Gln Lys Arg Ile Val Thr
                405                 410                 415
Glu Asn Lys Thr Asp Glu Glu Pro Gly Tyr Ile Lys Lys Cys Cys Lys
            420                 425                 430
Gly Phe Cys Ile Asp Ile Leu Lys Lys Ile Ser Lys Ser Val Lys Phe
        435                 440                 445
Thr Tyr Asp Leu Tyr Leu Val Thr Asn Gly Lys His Gly Lys Lys Ile
    450                 455                 460
Asn Gly Thr Trp Asn Gly Met Ile Gly Glu Val Val Met Lys Arg Ala
465                 470                 475                 480
Tyr Met Ala Val Gly Ser Leu Thr Ile Asn Glu Glu Arg Ser Glu Val
                485                 490                 495
Val Asp Phe Ser Val Pro Phe Ile Glu Thr Gly Ile Ser Val Met Val
            500                 505                 510
Ser Arg Ser Asn Gly Thr Val Ser Pro Ser Ala Phe Leu Glu Pro Phe
```

```
                515                 520                 525
Ser Ala Asp
    530

<210> SEQ ID NO 12
<211> LENGTH: 20
<212> TYPE: PRT
<213> ORGANISM: homo sapiens

<400> SEQUENCE: 12

Gly Tyr Ile Lys Lys Cys Cys Lys Gly Phe Cys Ile Asp Ile Leu Lys
1               5                   10                  15

Lys Ile Ser Lys
         20

<210> SEQ ID NO 13
<211> LENGTH: 21
<212> TYPE: PRT
<213> ORGANISM: artificial sequence
<220> FEATURE:
<223> OTHER INFORMATION: artificial sequence

<400> SEQUENCE: 13

Cys Gly Tyr Ile Lys Lys Cys Cys Lys Gly Phe Cys Ile Asp Ile Leu
1               5                   10                  15

Lys Lys Ile Ser Lys
             20

<210> SEQ ID NO 14
<211> LENGTH: 6237
<212> TYPE: DNA
<213> ORGANISM: homo sapiens

<400> SEQUENCE: 14
ttgaatttgc atctcttcaa gacacaagat taaaacaaaa tttacgctaa attggatttt      60
aaattatctt ccgttcattt atccttcgtc tttcttatgt ggatatgcaa gcgagaagaa     120
gggactggac attcccaaca tgctcactcc cttaatctgt ccgtctagag gtttggcttc     180
tacaaaccaa gggagtcgac gagttgaaga tgaagcccag agcggagtgc tgttctccca     240
agttctggtt ggtgttggcc gtcctggccg tgtcaggcag cagagctcgt tctcagaaga     300
gccccccccag cattggcatt gctgtcatcc tcgtgggcac ttccgacgag gtggccatca     360
aggatgccca cgagaaagat gatttccacc atctctccgt ggtacccccgg gtggaactgg     420
tagccatgaa tgagaccgac ccaaagagca tcatcacccg catctgtgat ctcatgtctg     480
accggaagat ccaggggggtg gtgtttgctg atgacacaga ccaggaagcc atcgcccaga     540
tcctcgattt catttcagca cagactctca ccccgatcct gggcatccac ggggggctcct     600
ctatgataat ggcagataag gatgaatcct ccatgttctt ccagtttggc ccatcaattg     660
aacagcaagc ttccgtaatg ctcaacatca tggaagaata tgactggtac atcttttcta     720
tcgtcaccac ctatttccct ggctaccagg actttgtaaa caagatccgc agcaccattg     780
agaatagctt tgtgggctgg agctagagg aggtcctcct actggacatg tccctggacg     840
atggagattc taagatccag aatcagctca agaaacttca aagccccatc attcttcttt     900
actgtaccaa ggaagaagcc acctacatct ttgaagtggc caactcagta gggctgactg     960
gctatgccta cacgtggatc gtgcccagtc tggtggcagg ggatacagac acagtgcctg    1020
cggagttccc cactggggctc atctctgtat catatgatga atgggactat ggcctccccg    1080
```

-continued

```
ccagagtgag agatggaatt gccataatca ccactgctgc ttctgacatg ctgtctgagc    1140
acagcttcat ccctgagccc aaaagcagtt gttacaacac ccacgagaag agaatctacc    1200
agtccaatat gctaaatagg tatctgatca atgtcacttt tgaggggagg aatttgtcct    1260
tcagtgaaga tggctaccag atgcacccga aactggtgat aattcttctg aacaaggaga    1320
ggaagtggga aagggtgggg aagtggaaag acaagtccct gcagatgaag tactatgtgt    1380
ggccccgaat gtgtccagag actgaagagc aggaggatga ccatctgagc attgtgaccc    1440
tggaggaggc accatttgtc attgtggaaa gtgtggaccc tctgagtgga acctgcatga    1500
ggaacacagt cccctgccaa aaacgcatag tcactgagaa taaaacagac gaggagccgg    1560
gttacatcaa aaaatgctgc aaggggttct gtattgacat ccttaagaaa atttctaaat    1620
ctgtgaagtt cacctatgac ctttacctgg ttaccaatgg caagcatggg aagaaaatca    1680
atggaacctg gaatggtatg attggagagg tggtcatgaa gagggcctac atggcagtgg    1740
gctcactcac catcaatgag gaacgatcgg aggtggtcga cttctctgtg cccttcatag    1800
agacaggcat cagtgtcatg gtgtcacgca gcaatgggac tgtctcacct tctgccttct    1860
tagagccatt cagcgctgac gtatgggtga tgatgtttgt gatgctgctc atcgtctcag    1920
ccgtggctgt ctttgtcttt gagtacttca gccctgtggg ttataacagg tgcctcgctg    1980
atggcagaga gcctggtgga ccctcttTca ccatcggcaa agctatttgg ttgctctggg    2040
gtctggtgtt taacaactcc gtacctgtgc agaacccaaa ggggaccacc tccaagatca    2100
tggtgtcagt gtgggccttc tttgctgtca tcttcctggc cagctacact gccaacttag    2160
ctgccttcat gatccaagag gaatatgtgg accaggtttc tggcctgagc gacaaaaagt    2220
tccagagacc taatgacttc tcacccccTT tccgctttgg gaccgtgccc aacggcagca    2280
cagagagaaa tattcgcaat aactatgcag aaatgcatgc ctacatggga aagttcaacc    2340
agaggggtgt agatgatgca ttgctctccc tgaaaacagg gaaactggat gccttcatct    2400
atgatgcagc agtgctgaac tatatggcag gcagagatga aggctgcaag ctggtgacca    2460
ttggcagtgg gaaggtcttt gcttccactg gctatggcat tgccatccaa aaagattctg    2520
ggtggaagcg ccaggtggac cttgctatcc tgcagctctt tggagatggg gagatggaag    2580
aactggaagc tctctggctc actggcattt gtcacaatga aagaatgag gtcatgagca    2640 gccagctgga cattgacaac atggcagggg tcttctacat gttgggggcg ccatggctc    2700 tcagcctcat caccttcatc tgcgaacacc ttttctattg gcagttccga cattgcttta    2760
tgggtgtctg ttctggcaag cctggcatgg tcttctccat cagcagaggt atctacagct    2820
gcatccatgg ggtggcgatc gaggagcgcc agtctgtaat gaactccccc accgcaacca    2880
tgaacaacac acactccaac atcctgcgcc tgctgcgcac ggccaagaac atggctaacc    2940
tgtctggtgt gaatggctca ccgcagagcg ccctggactt catccgacgg gagtcatccg    3000
tctatgacat ctcagagcac cgccgcagct tcacgcattc tgactgcaaa tcctacaaca    3060
acccgccctg tgaggagaac ctcttcagtg actacatcag tgaggtagag agaacgttcg    3120
ggaacctgca gctgaaggac agcaacgtgt accaagatca ctaccaccat caccaccggc    3180
cccatagtat tggcagtgcc agtccatcg atgggctcta cgactgtgac aacccaccct    3240
tcaccaccca gtccaggtcc atcagcaaga gccctgga catcggctc ccctcctcca    3300 agcacagcca gctcagtgac ctgtacggca aattctccct caagagcgac cgctacagtg    3360
gccacgacga cttgatccgc tccgatgtct ctgacatctc aacccacacc gtcacctatg    3420
ggaacatcga gggcaatgcc gccaagaggc gtaagcagca atataaggac agcctgaaga    3480
```

```
agcggcctgc ctcggccaag tcccgcaggg agtttgacga gatcgagctg gcctaccgtc    3540
gccgaccgcc ccgctcccct gaccacaagc gctacttcag ggacaaggaa gggctacggg    3600
acttctacct ggaccagttc cgaacaaagg agaactcacc ccactgggag cacgtagacc    3660
tgaccgacat ctacaaggag cggagtgatg actttaagcg cgactccatc agcggaggag    3720
ggccctgtac caacaggtct cacatcaagc acgggacggg cgacaaacac ggcgtggtca    3780
gcggggtacc tgcaccttgg gagaagaacc tgaccaacgt ggagtgggag gaccggtccg    3840
ggggcaactt ctgccgcagc tgtccctcca agctgcacaa ctactccacg acggtgacgg    3900
gtcagaactc gggcaggcag gcgtgcatcc ggtgtgaggc ttgcaagaaa gcaggcaacc    3960
tgtatgacat cagtgaggac aactccctgc aggaactgga ccagccggct gccccagtgg    4020
cggtgacgtc aaacgcctcc accactaagt accctcagag cccgactaat tccaaggccc    4080
agaagaagaa ccggaacaaa ctgcgccggc agcactccta cgacaccttc gtggacctgc    4140
agaaggaaga agccgccctg ccccgcgca gcgtaagcct gaaagacaag ggccgattca    4200
tggatgggag cccctacgcc cacatgtttg agatgtcagc tggcgagagc acctttgcca    4260
acaacaagtc ctcagtgccc actgccggac atcaccacca caacaacccc ggcggcgggt    4320
acatgctcag caagtcgctc taccctgacc gggtcacgca aaaccctttc atccccactt    4380
ttggggacga ccagtgcttg ctccatggca gcaaatccta cttcttcagg cagcccacgg    4440 tggcggggc gtcgaaagcc aggccggact ccgggccct tgtcaccaac aagccggtgg    4500
tctcggccct tcatggggcc gtgccagccc gtttccagaa ggacatctgt atagggaacc    4560
agtccaaccc ctgtgtgcct aacaacaaaa accccagggc tttcaatggc tccagcaatg    4620
ggcatgttta tgagaaactt tctagtattg agtctgatgt ctgagtgagg aacagagag    4680 gttaaggtgg gtacgggagg gtaaggctgt gggtcgcgtg atgcgcatgt cacggagggt    4740 gacggggtg aacttggttc ccatttgctc ctttcttgtt ttaatttatt tatgggatcc    4800
tggagttctg gttcctactg ggggcaaccc tggtgaccag caccatctct cctccttttc    4860
acagttctct ccttcttccc cccgctgtca gccattcctg ttcccatgag atgatgccat    4920
gggccctctc agcaggggag ggtagagcgg agaaggaag gctgcatgc gggcttcctc    4980 ctggtgtgga agagctcctt gatatcctct ttgagtgaag ctgggagaac caaaaagagg    5040
ctatgtgagc acaaaggtag cttttcccaa actgatcttt tcatttaggt gaggaagcaa    5100
aagcatctat gtgagaccat ttagcacact gcttgtgaaa ggaaagaggc tctggctaaa    5160
ttcatgctgc ttagatgaca tctgtctagg aatcatgtgc caagcagagg ttgggaggcc    5220
atttgtgttt atatataagc ccaaaaatgc ttgcttcaac cccatgagac tcgatagtgg    5280
tggtgaacag aacccaaggt cattggtggc agagtggatt cttgaacaaa ctggaaagta    5340
cgttatgata gtgtccccg gtgccttggg gacaagagca ggtggattgt gcgtgcatgt    5400
gtgttcatgc acacttgcac ccatgtgtag tcaggtgcct caagagaagg caaccttgac    5460
tctttctatt gtttctttca atatccccaa gcagtgtgat tgtttggctt atatacagac    5520
agagatggcc atgtattacc tgaattttgg ctgtgtctcc cttcatcctt ctggaataag    5580
gagaatgaaa attcttgata agaagattc tgtggtctaa acaaaaaag gcggtgagca    5640 atcctgcaag aacaaggtac ataaacaagt cctcagtggt tggcaattgt ttcaaccagt    5700
ttgaaccaag aactttccag gaaggctaaa gggaaaccga attttcacag ccatgattct    5760
tttgcccaca cttgggagca aaagattcta caaagctctt ttgagcattt agactctcga    5820
```

```
ctggccaagg tttggggaag aacgaagcca cctttgaaga agtaaggagt cgtgtatggt    5880
agggtaagtg agagaggggg atgtttccaa tgctttgatc ccttcttact taacctgaag    5940
ctagacgagc aggcttcttc cccccaaaac tgattacaac tgctacagag cagacagtta    6000
agagaaatga gcttgacctt taagagaaat gagctgcact ccatgagtgc agctctggag    6060
gtacgaaaag aggggaagag acttggaaat gggagacggg ggcagagagg gaccctccac    6120
cacctctttg ggcctggctc cctgggaatg tgacttgagc ccagagtgaa cactcttggt    6180
agaagcccct ctaccttcct gcaacacctt gtttccctct cagattgtac cattgag      6237

<210> SEQ ID NO 15
<211> LENGTH: 60
<212> TYPE: DNA
<213> ORGANISM: homo sapiens

<400> SEQUENCE: 15
ggttacatca aaaatgctg caaggggttc tgtattgaca tccttaagaa aatttctaaa      60

<210> SEQ ID NO 16
<211> LENGTH: 21
<212> TYPE: DNA
<213> ORGANISM: artificial sequence
<220> FEATURE:
<223> OTHER INFORMATION: artificial sequence

<400> SEQUENCE: 16
tcactgagaa taaaacagac g                                              21

<210> SEQ ID NO 17
<211> LENGTH: 21
<212> TYPE: DNA
<213> ORGANISM: artificial sequence
<220> FEATURE:
<223> OTHER INFORMATION: artificial sequence

<400> SEQUENCE: 17
tcacctatga cctttacctg g                                              21
```

ASSAY METHODS FOR IMMEDIATE DIAGNOSIS OF CAUSE OF STROKE

RELATION TO PRIOR APPLICATIONS

This application is a continuation of and claims priority to U.S. Utility application Ser. No. 11/076,074, filed Mar. 9, 2005 (currently pending), which is a continuation of U.S. Utility application Ser. No. 09/922,011, filed Aug. 2, 2001 (now issued as U.S. Pat. No. 6,896,872), which claims priority to U.S. Provisional Application No. 60/301,297, filed Jun. 27, 2001, and to U.S. Utility application Ser. No. 09/632,749, filed Aug. 4, 2000, of which U.S. Ser. No. 09/922,011 was a continuation-in-part.

BACKGROUND OF THE INVENTION

1. Field of the Invention

The present invention relates generally to the diagnosis, management and therapy of central nervous system disorders such as stroke, transient ishemic attack, and traumatic brain injury. In particular, the invention relates to methods and kits for evaluating these central nervous system disorders, in order to better respond to episodes of focal cerebral ishemia, and to best manage the risk associated with future acute incidences.

2. Background Information

Stroke or "brain attack" is clinically defined as a rapidly developing syndrome of vascular origin that manifests itself in focal loss of cerebral function. In more severe situations, the loss of cerebral function is global. A stroke occurs when the blood supply to the part of the brain is suddenly interrupted (ischemic) or when a blood vessel in the brain bursts, spilling blood into the spaces surrounding the brain cells (hemorrhagic). The symptoms of stroke are easy to spot: sudden numbness or weakness, especially on one side of the body; sudden confusion or trouble speaking or understanding speech; sudden trouble seeing in one or both eyes; sudden trouble walking; dizziness; or loss of balance or coordination. (National Institute of Neurological Disorders and Stroke, 2001). Stroke is the most common devastating neurologic disease in the world, and the third leading cause of death in world after heart disease and cancer. Despite recent progress understanding stroke mechanisms, stroke management is still not optimal for a number of reasons.

The importance of promptly diagnosing a stroke after symptoms appear cannot be overstated. Delays in diagnosis and medical intervention beyond 3 hours after stroke onset may contribute to clinical deterioration and disability. An early diagnosis enables doctors to more effectively choose the emergency intervention such as anti-platelet and/or neuroprotective therapy, and also to make better prognoses of disease outcome. Successful treatment of stroke requires rapid state diagnosis. The delay in achieving an accurate and certain diagnosis wastes the limited amount of time available in which the brain can respond to reperfusion, and significantly increases the risk of hemmorrhage after most of the permanent injury has occurred (Marler J. R. Annl. Emergency Med. 1999, 33: 450-451).

Unfortunately, however, many people who have a stroke either do not seek immediate medical care or suffer from delays in medical care even in countries where stroke care is advanced, such as the United States and Europe (Alberts M J, Hademenos G, Latchaw R E, et al. JAMA 2000; 23:3102-3109). Several clinical criteria can be employed to diagnose whether a patient is having a stroke, but even all these criteria do not always allow one to differentiate the episode from other disorders, such as epilepsy, syncope, and migraine (Toole J F. Cerebrovascular Disorders. 1999. Lippincott, Williams & Wilkins, New York, 5$^{th}$ Ed., 542 p). Moreover, progressing stroke is only partially predictable based on clinical and neuroimaging data that is currently available to neurologists.

Transient ischemic attack (TIA) is a short-lived episode of focal neurologic deficit which often precedes the cerebral infarction of a stroke. It occurs when the blood supply to part of the brain is briefly interrupted, and is typically accompanied by permanent brain damage (albeit less severe damage than normally results from a stroke). TIA symptoms, which usually occur suddenly, are similar to those of stroke but do not last as long. Most symptoms of a TIA disappear within an hour, although they may persist for up to 24 hours. Symptoms can include: numbness or weakness in the face, arm, or leg, especially on one side of the body; confusion or difficulty in talking or understanding speech; trouble seeing in one or both eyes; and difficulty with walking, dizziness, or loss of balance and coordination. (National Institute of Neurological Disorders and Stroke, 2001). Patients who have suffered a TIA have 9.5 times greater risk of having a future stroke than those who have not had a TIA, and about one third of patients who suffer a TIA will have an acute stroke in the future. (American Stroke Association, 2001). However, because the symptoms of TIA are short term, many patients do not recognize the event as a TIA or perceive the event as a warning of a potentially impending stroke.

Standard treatments to reduce the risk of future stroke include the use of antiplatelet agents, particularly aspirin. People with atrial fibrillation (irregular beating of the heart) may be prescribed anticoagulants. The most important treatable factors linked to TIAs and stroke are high blood pressure, cigarette smoking, heart disease, carotid artery disease, diabetes, and heavy use of alcohol. Lifestyle changes can often be implemented to reduce these factors. However, it is necessary to diagnose the TIA as a warning sign of impending stroke before such treatments can be administered. Therefore, a laboratory blood test to detect TIA or stroke, or the risk of suffering a TIA or stroke in the future, would be of tremendous benefit.

During the past 5 years a number of molecular and immunochemical assays have been evaluated for clinical use in neurology. (Schenone A. et. al. Current Opinion in Neurology. 1999, 12:603-604; Honnorat J. J. Neurol. Neurosurg. Psychiatry. 1996, 61:270-278). At present, the Thrombogene V and two Thrombx tests are available for diagnosing stroke/thrombosis from Athena Diagnostic. These tests evaluate the frequent deep vein thrombosis and hypercoagulation states of patients to evaluate the need for intravenous anticoagulant therapy. The Thrombogene V test detects the Factor V Leiden mutation by Polymerase Chain Reaction (PCR) in the blood of patients. The other two tests monitor changes of different blood coagulation markers: antithrombin III protein C, factor IX, and anticardiolipin antibodies (IgG, IgM, IgA) by use of ELISA technique. These tests thus reveal the hypercoagulation state as a result of a thrombotic events, such as stroke.

Stroke can be related to different types of venous thromboembolisms, which are common disorders with considerable morbidity and potential for mortality (Anderson, D.; Wells, P. Cur. Opinion in Hemat. 2000, 7:296-301). The biochemical marker: D-dimer, a breakdown product of a cross-linked fibrin blood clot that indicates the occurrence of plasmin mediated lysis of cross-linked fibrin, has been extensively evaluated for use in diagnostic tests for indicating acute venous thromboembolism. Indeed, a fully automated, semi-quantative latex agglutination assays that uses turbimetric or agglutination endpoints has been developed that provides results within 20 minutes with sensitivity between 89% and 95% (Roussi J.; Bentolila L.; Contribution of D-dimer determination in the exclusion of deep venus thrombosis in spinal cord injury patients. Spinal Cord,1999; v.37: p.548-552). Unfortunately, however, the presence of D-dimer may also be increased in other settings that result in fibrin generation, including recent surgery, hemmorhage, trauma, cancer, and pregnancy (Anderson D R., Wells P S.; Thromb. Haemost.; 1999; 82:878-886).

However, the foregoing tests do not elucidate upon the TIA/stroke mechanisms that are actually responsible for the damage associated with neurotoxic molecular events. It is necessary to find out specific and sensitive biomarkers which could be helpful to recognize initial brain damage and which could help to choose not only the appropriate anticoagulant treatment, but also emergency or regular neuroprotective therapy.

It is well known that two of the three leading causes of death, namely cardiovascular diaseses and stroke, are the end result of atherosclerosis. Thus, it is not surprising that several biochemical markers implicated in thromboembolic processes are also reported to be associated with stroke and stroke risk. Among these are homocysteine, cholesterol and LDL (Cerebrovascular Disorders ed. by J. E. Toole. Lippincott Williams & Wilkins. 1999, pp.34-35), which are also classified as risk factors to cardiovascular and cerebrovascular diseases. (Hankey G J., and Eikelboom J W. Lancet. 354: 407-413 (1999). Approximately one fourth of patients with symptomatic atherosclerosis have elevated plasma homocysteine levels caused by various factors. High levels of homocysteine may run in families with increased susceptibility to heart attack and stroke (Graham I. J. Ir. Call. Phys. Surg. 1995; 24:25-30). Elevated plasma homocysteine may be a causal and modifiable risk-factor for ischemic stroke, but the results of previous studies have been conflicting (Deulofeu V N R, Chamorro A, Piera C. Med Clin (Barc). 1998; 110:605-608; Yamamoto T, Rossi S, Stiefel M F, Doppenberg E, Zauner A, Bullock R, Marmarou A. Acta Neurochir. Suppl. (Wien) 1999; 75:17-19).

The neurotoxic effect of excitatory amino acids (glutamate, aspartate) in the brain has also been well documented. The results of this work show a correlation between glutamate content in the blood and the severity of acute ischaemia (Castillo J, Dávalos A, Naveiro J, Noya M. Stroke 1996, 27:1060-1065; Castillo J, Dávalos A, Noya M. Lancet. 1997; 349:79-83). Cerebral damage and its association with progressing stroke has been attributed to increased glutamate release, or low glutamate reuptake, both in animals and in humans (Dávalos A, Castillo J, Serena J, Noya M. Stroke 1997; 28:708-710).

However, only 56% of patients with progressing stroke are reported to have high glutamate content in their blood serum (Dávalos A., Toni D., Iweins F., et al., 1999, 30: 2631-2636). Moreover, even though glutamate is considered the strongest biochemical predictor of progressing stroke (Davalos A, and Castillo J. In Book: *Cerebrovascular Disease*. Current Med. Inc.: Philadelphia 2000 Chapter 16, pp. 169-181), this marker remains non-specific for TIA. Glutamate changes have also been observed in the blood of patients with epilepsy and other nervous system disorders (Meldrum B S. J. Nutrition. 2000, 130:1007S-1015S).

Over the last three decades substantial progress has been made in elucidating the mechanisms by which cerebral ischemia leads to brain damage. The cellular and molecular mechanisms of cerebral ischemia abnormalities have been better defined through the role of glutamate and glutamate receptors, one of the most distributed excitatory neuroreceptors in brain, in regulating of initial stages of brain damage. Indeed, numerous molecular investigators consider glutamate receptors to be one of the key biological receptors involved in the molecular mechanisms of TIA and stroke (Meldrum B S. J. Nutrition. 2000, 130:1007S-1015S). According to a leading hypothesis, ischemia-induced glutamate release activates these glutamate receptors. It has been shown that glutamate and homocysteine (the sulfinic analog of aspartate) activate the glutamate binding site of NMDA receptors and participate in neurotoxic processes (Lipton S. A., Kim W. K., Choi Y. B., Kumar S., et al. PNAS. 1997, 94:5923-5928).

Glutamate receptors are divided into two main groups: ionotropic and metabotropic. The ionotropic neuroreceptors are ligand-gated ion channels that are subdivided into NMDA, AMPA and kainate receptor subtypes. There are four NR2 subunits: NR2A, NR2B, NR2C and NR2D, which is responsible for $Ca^{2+}$-permeability regulation. NMDA receptors can be modified by ischemia, resulting in changes of ion permeability and/or ion selectivity.

Recent research findings indicate that the blood of patients with CNS disorders other than TIA or stroke exhibit properties of autoimmunization to products of nerve cell degradation (Vincent A., Oliver L., Pallace J. J Neuroimmun. 1999; 100:169-180). For example, a correlation between AMPA GluR1 autoantibodies and common epilepsy has been shown (Dambinova et al. J.Neurol. Sci. 1997; 152:93-97; Dambinova et al. J. Neurochem. 1998;71:2088-2093), as has a correlation between AMPA GluR 3 autoantibodies and Rasmussen's encephalitis (Rogers S W, Andrews P I, Gahring L C, et al. Science. 1995;265:648-651; Twyman R E, Gahring. L C, Spiess J, Rogers S W. Neuron. 1995; 14:755-762; Gahring L C, Twyman R I, Greenlee J E, Rogers S W. Mol. Med. 1995; 1:245-253).

In a similar vein, several researchers have reported an increase in NMDA receptor synthesis, the appearance of high levels of receptor antigen, and the generation of autoantibodies to the receptors during the initial stages of cerebral ishemia (Gusev et al., J.Neurol.& Psych. 1996, 5:68-72; Dambinova et al. J.Neurol.Sci. 1997, 152:93-97; Dambinova et al. J.Neurochem. 1998, 71:2088-2093). Acting on this research, one company developed a laboratory kit (cerebral ischaemia (CIS)-test) that detects autoantibodies to the N-terminus domain of the NR2A subunit in the blood of patients with TIA or stroke (Gusev E. I., Skvortsova V I, Alekseev A A, Izykenova G A, Dambinova S A. S. S Korsakov's J.Neurol.& Psych. 1996; 5:68-72). The N-terminus domain of the NR2A subunit of NMDA receptors was selected as the immunoreactive epitope on the basis of molecular biological and experimental studies showing that this epitope is the most immunoreactive region of the receptor (Dambinova S A, Izykenova G A. J.High Nervous Activity. 1997; 47:439-446).

More recently, researchers have reported a correlation between the effectiveness of a stroke treatment regimen and the levels of autoantibodies to the NR2A and NR2B subunits of NMDA. In particular, these researchers have reported increased titers of autoantibodies to the NR2A and NR2B subunits of NMDA in the blood of patients severely affected by stroke, and a reduction of the autoantibodies, accompanied by an improvement in neurological function, during therapy by glycine—a non-specific agonist of NMDA receptors (Gusev et. al. Cerebrovascular Diseases. 2000, 10:49-60). Patients that responded positively to glycine had lower autoantibody titers than patients who were not treated, and had levels of autoantibodies that were close to the levels of autoantibodies in control subjects.

Unfortunately, the use of NR2A and NR2B autoantibodies in the diagnosis of stroke or TIA does not provide a real-time assessment of the damage being done by a stroke or TIA. Rather, because of the time the immune system requires to mount an immune response, and to generate NR2A and NR2B autoantibodies, methods that test for these antibodies at best provide a delayed assessment of the extent and severity of stroke or TIA.

Investigators from Canada (Hill M. D., Jackowski G., Bayer N., Lawrence M., Jaeschke R. Can.Med.Assoc.J. 2000, 163:1139-1140) have proposed a new diagnostic laboratory assay for differentiating stroke subtype. They designed a preliminary prospective cohort study to test a panel of biochemical markers (neuron-specific enolase[NSE], myelin basic protein [MBP], S-100 [betta] protein and thrombomodulin [Tm]) in blood samples from patients with acute ischemic stroke. These markers were chosen because they cover important cellular components of the brain that might be damaged in acute stroke. The 4 biochemical markers were assayed using a standard ELISA technique.

The results of this investigation demonstrated elevated levels of NSE in 89% of the patients admitted in hospitals, Tm in 43%, MBP in 39% and S-100 [beta] in 32%. At least one of the markers was elevated on admission in 93% of the acute stroke patients. By stroke type, 100% of the patients with lacunar stroke, 100% of those with posterior circulation stroke and 90% of those with partial anterior circulation stroke had elevated NSE levels on admission. Conversely, none of the patients with lacunar stroke had en elevated S-100 [beta] level initially or subsequently. Peak levels of NSE, S-100 [beta] and MBP, but not of Tm, were significantly correlated with admission NIHSS scores ($p<0.05$).

For stroke, 3 hours is an outside limit for administering appropriate therapies. The focus must change from extensive evaluation before any action to a well-planned acute emergency therapy developed using an appropriate diagnostic strategy. Every future advance to improve the outcome after TIA /stroke will depend on a fast initial response-within minutes and not hours (Marler J. R. Annl. Emergency Med. 1999, 33:450-451). Therefore, it is especially important to develop a fast and simple method (within one hour) of detecting brain and blood biomarkers capable of recognizing the initial processes of TIA/stroke before irreperable ischemic damage ensues.

OBJECTS OF INVENTION

Therefore, it is an object of the invention to provide biochemical methods and kits for diagnosing central nervous system disorders such as TIA and stroke.

It is another object of the present invention to improve upon the accuracy of currently available methods for diagnosing TIA and stroke, and to more accurately diagnose TIA and stroke to the exclusion of other nervous system disorders or traumatic brain injury.

It is still another object of the present invention to provide methods of diagnosing stroke using biochemical markers that distinguish between hemorrhagic and ischemic stroke.

Still another object of the invention is to provide biochemical analyses of the extent and progression of TIA or stroke, or the infarction resulting from the TIA or stroke.

It is another object of the present invention to provide rapid biochemical methods and kits for diagnosing TIA and stroke, to provide real-time assessments of TIA or stroke, within a window of time that permits effective therapeutic intervention.

It is another object of the present invention to provide rapid and inexpensive biochemical methods and kits for diagnosing TIA and stroke, which can be performed at frequent intervals to monitor the progression of a TIA or stroke, or the effectiveness of therapy administered against TIA or stroke.

Still another object of the present invention is to provide diagnostic methods and kits for assessing the risk of incurring a TIA or stroke, and for monitoring the remission of risk factors for TIA or stroke.

Still another object of the invention is to provide a panel of rapid multiple panel of biomarkers for assessing the nature, severity and progression of TIA or stroke, and thereby to enable a more effective selection of intervention therapy.

SUMMARY OF THE INVENTION

It has unexpectedly been discovered that levels of circulating NMDA receptor proteins or fragments thereof can be assessed using diagnostic kits and processes, and that levels of these proteins or fragments can be used to clinically evaluate patients suffering from ishemic central nervous system disorders such as stroke or TIA. When analyzed in combination with other biomarkers for stroke and TIA, such as the thromboembolic marker homocysteine, or the excititory amino acid glutamate, these proteins can diagnose the existence of a stroke with remarkable accuracy (generally greater than 89%). In contrast, the efficacy of single parameters for early diagnosis of stroke is 58% for glutamate, 66% for homocysteine, and 79% for NMDA receptors. The rapid evaluation of these neural ischemic biomarkers in an emergency room setting will greatly enhance the confidence of physicians when diagnosing stroke or TIA, and significantly improve the speed at which therapy against the stroke or TIA can be administered.

The biomarkers also yield extensive evidence about the nature of the stroke or TIA and the type therapy which should be administered. For example, the respective levels of biomarkers can be evaluated to determine whether the patient is suffering an ishemic or hemmorhagic stroke, or whether the patient is suffering from a traumatic brain injury. The data from the biomarkers can also be used to monitor or evaluate the progression of the ishemic episode, as well as the damage that has resulted as a consequence of the ischemia. High levels of all parameters reflect the neurological deficit and may be also used for prognosis of disease outcome. Moreover, a relationship has been observed between the respective levels of the biomarkers and the degree of thromboembolic and neurotoxicity in brain processes under the stroke. Once again, these relationships can be put to extensive use when evaluating the choice of emergency therapy in short time frames, such as anti-platelet and neuroprotective therapy. The data can be used independently of other diagnostic strategies, but preferably forms an integral part of a comprehensive diagnostic strategy employing conventional diagnostic techniques.

The data obtained from the NMDA biomarkers, especially when combined with data from other biomarkers such as glutamate and homocysteine, can also be used to monitor the efficacy of a treatment regime. It has surprisingly been found that the NMDA biomarkers provide real time evidence of neurotoxicity, and that reductions in levels of circulating NR1A or NR2A NMDA receptors or fragments thereof correspond well with reductions in neurotoxic mechanisms. By obtaining data at appropriate intervals using rapid laboratory techniques such as latex agglutination, one is able to monitor the progression of the episode in response to the therapeutic regime.

A latex agglutination technique has also been developed which dramatically increases the speed of diagnosis obtained by the methods of this invention, and thereby improves the effectiveness of the methods in emergency-room settings. The technique can be adapted for use in the detection of NMDA receptors, homocysteine, glutamate, or any other suitable biomarker against central nervous system disorders. Using the latex agglutination technique, one is able to provide real-time biochemical diagnosis and monitoring of TIA/stroke patients (within about 30 minutes), and thereby dramatically improve the effectiveness of response to TIA/stroke. This is surprising because these biomarkers are naturally occurring and, in contrast to viruses for which latex agglutination methods were originally developed, show much lower strengths of association with their corresponding antibodies.

This semi-quantitative method gives reliable data quickly in a format that is simple for interpretation. Surprisingly, the technique shows greater accuracy than even well established methods based upon HPLC and ELISA. The application of the latex agglutination technique to the analysis of brain biomarkers for stroke will decrease the cost of analysis, provide the opportunity to monitor real-time progress of a treatment procedure, and allow physicians to determine the efficacy of medication administered in the treatment of TIA or stroke.

The methods of the present invention also can be employed in a non-emergency setting, when evaluating the risk that an individual will suffer a stroke or TIA. In addition, based upon results showing an increased risk of suffering TIA or stroke, prevention therapy can be administered, and the effectiveness of the therapy monitored using the methods of the present invention.

The invention also relates to indirect methods for measuring levels of NR2A and NR2B NMDA receptor proteins or fragments thereof. Thus, analytical techniques can be used to evaluate indirect measures of NR2A and NR2B NMDA receptor proteins or fragments thereof, such as autoantibodies specific for the proteins, or cDNA that encodes for the proteins.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE INVENTION

The present invention may be understood more readily by reference to the following detailed description of preferred embodiments of the invention and the Examples included therein. Before the present methods and techniques are disclosed and described, it is to be understood that this invention is not limited to specific analytical or synthetic methods as such may, of course, vary. It is also to be understood that the terminology used herein is for the purpose of describing particular embodiments only and is not intended to be limiting.

Definitions and Use of Terms

As used in this specification and in the claims which follow, the singular forms "a," "an" and "the" include plural referents unless the context clearly dictates otherwise. Thus, for example, reference to "a fragment" includes mixtures of fragments, reference to "an cDNA oligonucleotide" includes more than one oligonucleotide, and the like.

An analogue of a protein, peptide, or polypeptide means a protein, peptide, or polypeptide that contains one or more amino acid substitutions, deletions, additions, or rearrangements. For example, it is well known in the art of protein biochemistry that an amino acid belonging to a grouping of amino acids having a particular size or characteristic (such as charge, hydrophobicity, and hydrophilicity) can often be substituted for another amino acid without altering the activity of the protein, particularly in regions of the protein that are not directly associated with biological activity. Thus, an analogue of an NMDA receptor or fragment thereof is useful in the present invention if it includes amino acid substitutions, deletions, additions or rearrangements at sites such that antibodies raised against the analogue are still specific against the NMDA receptor or fragment.

Preferably, an NMDA analogue has at least 80%, 85%, 90%, or 95% amino acid identity with naturally occurring NMDA. Amino acid identity is defined by a analoguey comparison between the analogue and naturally occurring NMDA. The two amino acid sequences are aligned in such a way that maximizes the number of amino acids in common along the length of their sequences; gaps in either or both sequences are permitted in making the alignment in order to maximize the number of common amino acids. The percentage amino acid identity is the higher of the following two numbers: (1) the number of amino acids that the two polypeptides have in common with the alignment, divided by the number of amino acids in the NMDA analogue or fragment thereof, multiplied by 100, or (2) the number of amino acids that the two polypeptides have in common with the alignment, divided by the number of amino acids in naturally occurring NMDA or fragment thereof, multiplied by 100.

NMDA derivatives, and derivatives of NMDA fragments, include naturally occurring NMDA and NMDA analogues and fragments thereof that are chemically or enzymatically derivatized at one or more constituent amino acids, including side chain modifications, backbone modifications, and N- and C- terminal modifications, by for example acetylation, hydroxylation, methylation, amidation, phosphorylation or glycosylation. The term also includes NMDA salts such as zinc NMDA and ammonium NMDA.

A protein or peptide is measured "directly" in the sense that the protein or peptide is itself measured in the biological sample, as opposed to some other indirect measure of the protein or peptide such as autoantibodies to the protein or peptide, or cDNA associated with the expression of the protein or peptide.

The term "antibody" is intended to be synonymous with "immunoglobulin." As used herein, the term "antibody" is meant to include both the native antibody, and biologically active derivatives of antibodies, such as, for example, Fab', F(ab')$_2$ or Fv as well as single-domain and single-chain antibodies. A biologically active derivative of an antibody retains the ability to bind antigen.

General Discussion

The present disclosure describes diagnostic and therapeutic applications that result from the realization that genetic or accidental increase of NMDA receptors synthesis in the brain reflects a neurological ischemic deficit, and may be used for early diagnoses of stroke or TIA. NMDA receptors that are abnormally expressed in the brain are quickly metabolized and, following penetration of the blood brain barrier, these metabolic destruction products enter the circulatory system. The immune system recognizes these peptides and protein fragments as foreign antigens and responds by generating autoantibodies to them.

In one aspect of the present invention, the correlation between increased NMDA receptor synthesis, and the appearance of high levels of the receptors in blood sera of individuals during the initial stages of cerebral ischemia, is used for diagnostic and therapeutic applications. Experiments in rats with focal ischemia have demonstrated that NR2A mRNA expression in the cortex and hippocampus can be measured within two hours of the onset of the ischemic episode, and thus provide an opportunity for real time measurement of ischemic processes and damage resulting therefrom. At the same time, meaningful expression of NR2C and NR2D mRNA is not observed in brain structures that showed no changes in NR1 mRNA expression in rat ischemic brain. These changes in NR2-receptor mRNA expression in the early stages of ischemia are observed prior to morphological evidence of neuronal damage or appearance of autoantibodies to them in blood serum specimens.

Thus, in one aspect the present invention provides a method for diagnosing a central nervous system disorder comprising measuring the level of NR2A and/or NR2B NMDA receptor or fragment thereof in a biological sample. Elevated levels of NR2A and NR2B NMDA receptors are specific to brain injury, and are expressed in ischemic brain tissue at higher rates than other NMDA receptors, and thus are uniquely suited for assessing ischemic brain episodes such as TIA or stroke. Baseline levels for determining whether the measured levels are elevated, and hence indicative of a central nervous system disorder, can be obtained from population norms or, preferably, from a patient's own test history.

The biological sample tested for the receptor or fragment can be derived from blood, urine, blood plasma, blood serum, cerebrospinal fluid, saliva, perspiration, or brain tissue. In a preferred embodiment, the biological sample is a blood sample. In an even more preferred embodiment the biological sample is a blood sample diluted to a ratio of from about 1:2 to about 1:32 (v:v).

Immunoassay techniques are generally preferred for measuring the proteins or peptides of the present invention, as discussed in greater detail herein, although other analytical techniques are also available as known to those skilled in the art, such as HPLC. The amino acid sequences of the NR2A and NR2B subunits, and antigenic fragments thereof, are recited in SEQ ID NOS.1, 2, 3, 10, 11, and 12, and any fragment of these sequences can be employed in methods for directly detecting the receptors as long as sufficient antigenicity is maintained. However, when using immunoassays it has been found that the antigenic determinants are concentrated in the N-terminal domain of the NR2A and/or NR2B NMDA receptor, and that antibodies raised against the N-terminal domains and fragments thereof should be employed for optimal test results. The inventors have sequenced the amino acid chain of the N-terminal domains for these receptors, and set forth the sequences as SEQ ID NOS. 2 and 11, respectively, at the end of this document.

In a preferred embodiment, other biomarkers of central nervous system disorders are also measured to improve the accuracy of the diagnosis, and to provide further information about the nature, severity, or progression of the disorder. Particularly useful markers are directly implicated in the NMDA receptor pathway, and include naturally occurring agonists and antagonists of the NMDA receptors. An exemplary antagonist is glycine. Exemplary agonists include glutamate, polyglutamate, aspartate, polyaspartate, homocysteine, and polyhomocysteine. A particularly preferred agonist for measuring the activity of the receptors is glutamate or polyglutamate.

In another embodiment, thromboembolic biomarkers are measured to obtain a simultaneous reading of the likelihood for clotting in the brain. Exemplary thromboembolic biomarkers include homocysteine or polyhomocysteine.

Titers of higher than 2.63 for combined levels of NR2A and NR2B, especially when combined with titers higher than 3.34 for glutamate and/or 2.23 for homocysteine, are remarkably predictive of the occurrence of stroke and typically justify immediate therapeutic intervention for the TIA or stroke or risk of stroke. These titers can be translated into absolute concentrations by reference to the examples hereof.

The methods of the present invention are preferably performed by directly measuring the levels of NR2A and/or NR2B biomarkers in a selected biological sample, using immunoassay techniques employing antibodies raised against the biomarkers, or through quantitative techniques such as HPLC. However, it is also possible to measure the presence of the NR2A and/or NR2B biomarkers indirectly. This can be done by directly measuring autoantibodies of the biomarkers, or by directly measuring the cDNA nucleic acid intermediates involved in expression of these biomarkers. If autoantibodies are measured, they are preferably measured using one or more antigenic fragments of the NR2A and/or NR2B receptors as the target of the antibody, as opposed to a whole NR2A and/or NR2B protein. Healthy persons generally have NR2A autoantibodies in an amount of about 1.0-2.0 ng/ml. Healthy persons generally have NR2A cDNA levels of about 1.0-1.5 pg/ml.

Latex Agglutination and Other Diagnostic Techniques

A number of immunoassays can be employed in accordance with the principles of the present invention. Examples include radioimmunoassays, enzyme immunoassays (e.g. ELISA), immunofluorescence, immunoprecipitation, latex agglutination, hemagglutination, and histochemical tests. A particularly preferred method, however, because of its speed and ease of use, is latex agglutination.

Latex agglutination assays have been described in Beltz, G. A. et al., in Molecular Probes: Techniques and Medical Applications, A. Albertini et al., eds., Raven Press, New York, 1989, incorporated herein by reference. In the latex agglutination assay, antibody raised against a particular biomarker is immobilized on latex particles. A drop of the latex particles is added to an appropriate dilution of the serum to be tested and mixed by gentle rocking of the card. With samples lacking sufficient levels of the biomarkers, the latex particles remain in suspension and retain a smooth, milky appearance. However, if biomarkers reactive with the antibody are present, the latex particles clump into visibly detectable aggregates.

An agglutination assay can also be used to detect biomarkers wherein the corresponding antibody is immobilized on a suitable particle other than latex beads, for example, on gelatin, red blood cells, nylon, liposomes, gold particles, etc. The presence of antibodies in the assay causes agglutination, similar to that of a precipitation reaction, which can then be detected by such techniques as nephelometry, turbidity, infrared spectrometry, visual inspection, colorimetry, and the like.

The term latex agglutination is employed generically herein to refer to any method based upon the formation of detectable agglutination, and is not limited to the use of latex as the immunosorbent substrate. While preferred substrates for the agglutination are latex based, such as polystyrene and polypropylene, particularly polystyrene, other well-known substrates include beads formed from glass, paper, dextran, and nylon. The immobilized antibodies may be covalently, ionically, or physically bound to the solid-phase immunoadsorbent, by techniques such as covalent bonding via an amide or ester linkage, ionic attraction, or by adsorption. Those skilled in the art will know many other suitable carriers for binding antibodies, or will be able to ascertain such, using routine experimentation.

Thus, in one embodiment, the method of measuring the NR2A and/or NR2B NMDA receptor, fragment thereof, or other biomarker is by latex agglutination comprising:

(i) contacting the biological sample with poly- or monoclonal antibodies bound on an agglutinating carrier to target biomakers for a sufficient time period and under conditions to promote agglutination; and (ii) reading a signal generated from the agglutination; wherein the amount of signal detected correlates to the titer of biomarkers present in the sample.

The reaction is preferably read macroscopically against a dark background for a sufficient time period. The method preferably yields a clinically useful reading within about 30 minutes or less.

It has been experimentally found that latex beads having a mean diameter of from about 0.25 to about 0.4 μm are particularly preferred in the practice of this invention. The poly- or monoclonal antibodies are preferably present in a ratio with the latex beads of about 1:1.

Latex beads having the foregoing characteristics can be prepared generally by adding antibodies to the target biomarker to a carrier solution that contains a 1% concentration (by weight) of latex beads, until the concentration of the antibodies in the carrier solution reaches about 2 mg/ml, and allowing the ingredients a sufficient time to covalently link, typically about 1 hour, in the presence of a linking agent such as glutaraldehyde.

Conventional methods can be used to prepare the antibodies. For example, by using a peptide of a NMDA protein, polyclonal antisera or monoclonal antibodies can be made using standard methods. A mammal, (e.g., a mouse, hamster, or rabbit) can be immunized with an immunogenic form of the peptide (preferably the NR2A and/or NR2B receptor, an antigenic determinant of the NR2A and/or NR2B receptor, or an analogue or derivative thereof) which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be administered and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495-497 (1975)) as well as other techniques such as the human B-cell hybridoma technique (Kozbor et al., Immunol. Today 4, 72 (1983)), the EBV-hybridoma technique to produce human monoclonal antibodies (Cole et al. Monoclonal Antibodies in Cancer Therapy (1985) Allen R. Bliss, Inc., pages 77-96), and screening of combinatorial antibody libraries (Huse et al., Science 246, 1275 (1989)]. Hybridoma cells can be screened immunochemically for production of antibodies specifically reactive with the peptide and the monoclonal antibodies can be isolated. Therefore, the invention also contemplates hybridoma cells secreting monoclonal antibodies with specificity for NR2A or NR2B NMDA proteins or fragments thereof as described herein.

When the NR2A and/or NR2B receptors are detected indirectly, by measuring the cDNA expression of the NR2A and/or NR2B receptors, the measuring step in the present invention may be carried out by traditional PCR assays such as cDNA hybridization, Northern blots, or Southern blots. These methods can be carried out using oligonucleotides encoding the polypeptide antigens of the invention. Therefore, in one embodiment the methods are performed employing oligonucleotides that encode the amino acid sequence of SEQ ID NO: 2, which is preferably represented by nucleotides 371-1978 of SEQ ID NO: 6. More preferably, the nucleic acid construct comprises a oligonucleotide consisting of a nucleotide sequence encoding the amino acid sequence of SEQ ID NO: 3, which is preferably represented by oligonucleotides 1790-1852 of SEQ ID NO: 7.

Thus, in one embodiment the methods of this invention include measuring an increase of NR2A and/or NR2B cDNA expression by contacting the total DNA isolated from a biological sample with oligonucleotide primers attached to a solid phase, for a sufficient time period. In another preferred embodiment, NR2A and/or NR2B cDNA expression is measured by contacting an array of total DNA bound to a solid matrix with a ready-to-use reagent mixture containing oligonucleotide primers for a sufficient time period. Expressed NR2A cDNA is revealed by the complexation of the cDNA with an indicator reagent that comprises a counterpart oligonucleotide to the cDNA attached to a signal-generating compound. The signal-generating compound is preferably selected from the group consisting of horseradish peroxidase, alkaline phosphatase, urinase and non-enzyme reagents. The signal-generating compound is most preferably a non-enzyme reagent.

In a preferred embodiment, the solid phase is a polymer matrix. More preferably, the polymer matrix is polyacrylate, polystyrene, or polypropylene. In one preferred embodiment the solid phase is a microplate. In another preferred embodiment, the solid phase is a nitrocellulose membrane or a charged nylon membrane.

As mentioned above, the methods of performing the present invention also may be performed by measuring the levels of autoantibodies specific for the NR2A and/or NR2B subunits. These autoantibodies may be measured by any suitable immunoassay such as, for example, a radioimmunoassay, an immunofluorescence assay, an enzyme-linked immunosorbent assay (ELISA), an immunocytochemical assay, and immunoblotting. In a preferred embodiment, the antigen to which the anti-NR2A and/or NR2B autoantibodies bind is a polypeptide or protein fragment of the N-terminal domain of the NR2A and/or NR2B receptor. More preferably, the antigen comprises a polypeptide or protein fragment of amino acid SEQ ID NO: 2, 3, 4, 11, 12, or 13, or a suitable analogue or derivative thereof.

Thus, in yet another embodiment the methods of the present invention are performed by measuring the levels of anti-NR2A and/or anti-NR2B autoantibodies, by contacting a biological sample with a polypeptide or protein fragment of the NR2A and/or NR2B receptor (preferably the N-terminal domain) (or an analogue or derivative thereof) attached to a solid phase, for a sufficient time period and under conditions to allow a complex to form between any NR2A and/or NR2B autoantibodies which may be present in the sample and the polypeptide or protein fragment, contacting the complex with an indicator reagent comprising a secondary antibody specific for the species of the mammal attached to a signal-generating compound (or for the polypeptide or protein fragment); and measuring the signal generated. The peptide can be obtained directly from biological samples, by recombinant DNA techniques, or by direct chemical synthesis. The signal-generating compound is preferably selected from horseradish peroxidase, alkaline phosphatase, and urinase. More preferably, the signal-generating compound is horseradish peroxidase. Most preferably, the indicator reagent is rabbit anti-human IgG attached to horseradish peroxidase. The amount of signal detected is correlated to the amount of anti-NR2A and/or NR2B autoantibodies present in the biological sample.

In this method it is preferred that the solid phase be a polymer matrix. More preferably, the polymer matrix is selected from the group consisting of polyacrylate, polystyrene, and polypropylene. In one preferred embodiment the solid phase is a microplate. In another preferred embodiment, the solid phase is a nitrocellulose membrane or a charged nylon membrane.

The immunosorbent of the present invention for measuring levels of autoantibody can be produced as follows. A fragment of the receptor protein is fixed, preferably by covalent bond or an ionic bond, on a suitable carrier such as polystyrene or nitrocellulose. If the standard polystyrene plate for immunological examinations is employed, it is first subjected to the nitration procedure, whereby free nitrogroups are formed on the plate surface, which are reduced to amino groups and activated with glutaric dialdehyde serving as a linker. Next the thus-activated plate is incubated with about 2 to 50 nM of the target peptide for the purpose of chemically fixing the respective immunogenic fragment of the receptor protein for a time and at a temperature sufficient to assure fixation (i.e. for about 16 hours at 4° C.).

The amount of protein below 2 nM affects adversely the reliability of the findings, whereas its amount exceeding 50 nM is inexpedient due to an increase in the nonspecific binding of autoantibodies with the immunosorbents. The plate is then washed with an aqueous solution of sodium boron hydride and an aqueous solution of sodium chloride, vacuum-dried enclosed in a hermetically sealed package, and put under storage at 4° C.

It is also practicable to produce the immunosorbent by fixing the respective fragment of the receptor protein on nitrocellulose strips by virtue of ionic interaction. The respective fragment of the receptor protein isolated from the mammals' brain is applied to nitrocellulose and incubated for 15 min at 37° C. Then nitrocellulose is washed with a 0.5% solution of Tween-20, and the resultant immunosobent is dried at room temperature and stored in dry place for one year period.

Emergency Room Diagnosis and Prognosis

As mentioned above, the methods of the present invention are especially well suited for use in emergency room settings. There are two reasons for this. First, the method is extremely useful in an emergency room setting because NR2A and NR2B NMDA receptor levels are elevated at a very early stage of ishemic insult, and thus provide a real time indication of neurotoxic events. This is in contrast to autoantibodies which require that an immune response first be mounted by the insulted organism.

The second reason the method is useful in an emergency room setting is the speed and ease with which the latex agglutination procedure can be employed. Using the latex agglutination processes described herein, one is able to turn laboratory results around often in less than 30 or even 20 minutes. Thus, using the methods of the present invention real-time data can be obtained that permits a therapeutic response within the window for an effective response to stroke.

Therefore, in one embodiment the invention provides a method for diagnosing the existence of a central nervous system disorder such as TIA or stroke, further comprising withdrawing the biological sample from a human subject, wherein the biological sample is withdrawn within three hours of the onset of symptoms of the central nervous system disorder. In still another embodiment of the invention, the amount of time elapsed between withdrawing the biological sample from the subject, and detecting or measuring the presence or quantity of the NR2A and/or NR2B NMDA receptor, is less than about one hour, 45 minutes, or 30 minutes.

One of the principal advantages of the present invention is the ability to distinguish ischemic episodes such as stroke from other brain injuries such as traumatic brain injury. Thus, in another embodiment, the invention provides a method for diagnosing the existence of TIA or stroke further comprising evaluating from the level of NR2A and/or NR2B NMDA receptor whether the brain injury is a traumatic brain injury or stroke/TIA, and administering traumatic brain injury or stroke/TIA therapy as appropriate.

Another advantage of the methods of the present invention which is extremely useful in an emergency room setting, is the ability to determine from the test data the type of stroke involved. In particular, if a stroke is suspected, the method will help diagnose whether the stroke is an ischemic or hemorrhagic insult. Thus, in another embodiment the invention provides a method for diagnosing the existence of TIA or stroke further comprising, when the diagnosis confirms a stroke, evaluating from the level of NR2A and/or NR2B NMDA receptor whether the stroke is ischemic or hemmorhagic and administering ischemic or hemmorhagic stroke therapy as appropriate.

Another advantage of the present invention is the ability to evaluate infarction volume and extent of neurotoxicity from NMDA expression data. NMDA receptor expression research in an animal model of middle carotid artery occlusion has been employed to demonstrate such correlation. Thus, in still another embodiment the invention provides a method for diagnosing the existence of TIA or stroke further comprising, if TIA and/or stroke is confirmed, evaluating from the level of NR2A and/or NR2B NMDA receptor cranial infarct volume, and administering therapy appropriate to the infarct volume.

Moreover, one can periodically repeat the procedure, to provide continuous monitoring of a patient's state as interventional therapy is administered, to monitor the effectiveness of a particular therapeutic regime. In this embodiment, it is preferable for the mammal to be concurrently undergoing treatment for the disorder. More preferably, the samples are collected at intervals from about 20 min to about 1 month. Even more preferably, the interval is from about 20 min. to about 2 hours. Most preferably the samples are collected at an interval of about 30 minutes. Thus, in still another embodiment the invention provides a method for diagnosing the progression of TIA or stroke further comprising detecting or measuring the presence or quantity of a NR2A and/or NR2B NMDA receptor in a biological sample one or more additional times, at a frequency of less than about 6 hours.

Primary Care Physician Setting

In another application the method is used in a clinical setting to determine an individual's risk of stroke, or to monitor the effectiveness of risk reduction therapies. As mentioned above, a number of therapies can be employed to reduce the risk of stroke in an individual. The use of antiplatelet agents, particularly aspirin, is a standard treatment for patients at risk for stroke. People with atrial fibrillation (irregular beating of the heart) may be prescribed anticoagulants. The most important treatable factors linked to TIAs and stroke are high blood pressure, cigarette smoking, heart disease, carotid artery disease, diabetes, and heavy use of alcohol. Medical help is available to reduce and eliminate these factors. Lifestyle changes such as eating a balanced diet, maintaining healthy weight, exercising, and enrolling in smoking and alcohol cessation programs can also reduce these factors. When these therapies are administered it is desirable to determine the effectiveness of the therapy.

Therefore, in one embodiment the invention provides a method for evaluating an individual's risk for TIA or stroke comprising measuring levels of NR2A and/or NR2B NMDA receptors or fragments thereof in a biological sample from the individual, and comparing the levels to a baseline level. In one embodiment the baseline levels are derived from population averages. In another embodiment the baseline levels are derived from the individual's own medical history.

In another embodiment the method is performed more than once to monitor the reduction or increase in risk for stroke or TIA, optionally in conjunction with the administration of risk reduction therapy. In one embodiment the method is performed at a frequency of from about one week to about six months. In another embodiment the method is performed at a frequency of from about one month to about three months.

In a particularly preferred embodiment other biomarkers are also measured to assess the risk for stroke or TIA. Particularly preferred biomarkers for risk of stroke or TIA are glutamate and homocysteine.

Novel Kits of the Present Invention

In another embodiment the invention provides kits for diagnosing central nervous system disorders such as TIA, stroke, and traumatic brain injury. NR2A and/or NR2B antibodies or antigens may be incorporated into immunoassay diagnostic kits depending upon whether autoantibodies or NMDA receptors are being measured. A first container may include a composition comprising an antigen or antibody preparation. Both antibody and antigen preparations should preferably be provided in a suitable titrated form, with antigen concentrations and/or antibody titers given for easy reference in quantitative applications.

The kits may also include an immunodetection reagent or label for the detection of specific immunoreaction between the provided antigen and/or antibody, as the case may be, and the diagnostic sample. Suitable detection reagents are well known in the art as exemplified by radioactive, enzymatic or otherwise chromogenic ligands, which are typically employed in association with the antigen and/or antibody, or in association with a second antibody having specificity for first antibody. Thus, the reaction is detected or quantified by means of detecting or quantifying the label. Immunodetection reagents and processes suitable for application in connection with the novel methods of the present invention are generally well known in the art.

The reagents may also include ancillary agents such as buffering agents and protein stabilizing agents, e.g., polysaccharides and the like. The diagnostic kit may further include where necessary agents for reducing background interference in a test, agents for increasing signal, apparatus for conducting a test, calibration curves and charts, standardization curves and charts, and the like.

In a more particular aspect the invention relates to a rapid multiple panel containing antibodies to the thromboembolic and neurotoxicity biomarkers glutamate, homocysteine and NMDA receptors that employs latex agglutination. Thus, in one embodiment the invention provides a kit for diagnosing central nervous system disorders comprising: (1) an agglutinating immunosorbent for NR2A and/or NR2B NMDA receptors or fragments thereof, and (2) a control such as saline or a known concentration of NR2A and/or NR2B receptor or fragment thereof In a more preferred embodiment the kit further comprises an agglutinating immunosorbent for another biomarker for TIA/stroke, such as an agonist or antagonist of NR2A and/or NR2B, a thromboembolic marker, or more particularly glutamate or polyglutamate, and/or an agglutinating homocysteine or polyhomocysteine. The agglutinating immunosorbent is preferably of the type discussed in greater detail above.

In another embodiment the invention relates to a kit for detecting NR2A and/or NR2B receptors or fragments thereof that does not employ latex agglutination. Thus, in another embodiment the invention provides a kit for diagnosing central nervous system disorders comprising: (1) an immunosorbent for NR2A and/or NR2B NMDA receptors or fragments thereof, and (2) an indicator reagent comprising secondary antibodies attached to a signal generating compound. The secondary antibodies can be specific for the receptor or fragment, or for the primary antibodies in the immunosorbent. In a preferred embodiment the kits further comprise an immunosorbent for glutamate or polyglutamate, and/or an immunosorbent for homocysteine or polyhomocysteine, and secondary antibodies against the glutamate and/or homocysteine, or to the primary antibodies on the immunosorbents against the glutamate or homocysteine. The immunosorbent preferably comprises anti-antibodies for the biomarkers bound to a solid support.

In another aspect the present invention relates to a test-kit that relies upon PCR amplification for measuring NR2A and/or NR2B levels. Thus, in another embodiment the invention provides a kit comprising: (a) one or more oligonucleotide primers (preferably of SEQ ID NO: 8) attached to a solid phase, (b) indicator reagent attached to a signal-generating compound capable of generating a detectable signal from oligonucleotides, and (c) a control sample (i.e. template cDNA). The reagents may also include ancillary agents such as buffering agents, polymerase agents, and the like. The diagnostic kit may further include, where necessary, other members of the signal-producing system of which system the detectable group is a member (e.g., enzyme and non-enzyme substrates), agents for reducing background interference in a test, agents for increasing the signal, apparatus for conducting a test, and the like.

In another embodiment of test-kit comprises (a) a solid phase to which biological fluids for receiving total DNA including NR2A cDNA could be attached, (b) oligonucleotide primers, preferably in a ready-to-use PCR buffer, and (c) a control sample (i.e. template cDNA). Ancillary agents as described above may similarly be included.

In another embodiment the invention provides a diagnostic kit for detecting NR2A and/or NR2B autoantibodies comprising (a) a polypeptide of the N-terminal domain of the NR2A and/or NR2B receptor, fragment thereof, or analog or derivative thereof, (b) an indicator reagent comprising a secondary antibody specific for the autoantibody or the polypeptide attached to a signal-generating compound; and (c) a control sample, such as a known concentration of NR2A and/or NR2B polyclonal antibodies. The reagents may also include ancillary agents such as buffering agents and protein stabilizing agents, e.g., polysaccharides and the like. The diagnostic kit may further include, where necessary, other members of the signal-producing system of which system the detectable group is a member (e.g., enzyme and non-enzyme substrates), agents for reducing background interference in a test, agents to increase the signal, apparatus for conducting a test, calibration and standardization information or instructions, and the like.

Novel Compositions of the Invention

The methods of the present invention rely upon a series of novel compositions which themselves form a part of the invention. Thus, in one series of embodiments the invention provides an isolated polypeptide fragment of the NR2A and/or NR2B NMDA receptor, comprising:

1. An antigenic determinant of the NR2A NMDA receptor,
2. An antigenic determinant of the NR2B NMDA receptor,
3. The N-terminal domain of the NR2A NMDA receptor,
4. The N-terminal domain of the NR2B NMDA receptor,
5. SEQ ID NO. 2,
6. SEQ ID NO. 3,
7. SEQ ID NO. 4,
8. SEQ ID NO. 11,
9. SEQ ID NO. 12, and
10. SEQ D NO. 13, or an antigenic fragment, analog, or derivative thereof. In another series of embodiments the invention provides any of the foregoing polypeptides linked covalently to a distinct antigenic determinant, such as human serum albumin. In still another series of embodiments the invention provides any of the foregoing polypeptides linked to any of the immunosorbent materials discussed above. The immunosorbent can be in the form of a bead for latex agglutination, in the size ranges discussed above, or in the form of a synthetic plate for conventional immunoassay analysis. The polypeptide can be linked to the immunosorbent using any conventional means of linkage, including covalent linkage, ionic linkage, and adsorption.

In another series of embodiments the present invention relates to the novel monoclonal and polyclonal antibodies specific for and/or raised against the foregoing polypeptides, including the foregoing polypeptides linked to distinct antigenic determinants. Thus, in one embodiment the invention provides non-human antibodies against any of the foregoing peptides or polypeptides or antigenic fragment, analog, or derivative thereof. In another embodiment the invention provides immunosorbents to which such antibodies are linked.

In another series of embodiments the present invention provides oligonucleotides that encode the foregoing peptides and polypeptides and fragments, analogs, and derivatives thereof, and to recombinant expression vectors that include such oligonucleotides. Such oligonucleotides include, without limitation, the oligonucleotides defined by SEQ ID NO: 6, 7, 14, and 15, and fragments thereof which encode antigenic determinants.

In still another embodiment the present invention relates to isolated oligonucleotide sequences that are useful in the cDNA PCR analytical techniques of the present invention. Thus, the invention further provides oligonucleotides comprising the nucleotide sequences of SEQ ID NOS: 7, 8, 9, 15, 16, and 17.

BRIEF DESCRIPTION OF THE SEQUENCE LISTINGS

The features, aspects, and advantages of the present invention will become better understood with regard to the following sequence listings where, in the sequence the recited amino acid position numbering reflects that used throughout this document.

SEQ ID NO: 1. shows the full-length amino acid sequence of the mature NR2A receptor subunit, as follows:

Sequence Listing

```
PEPTIDE
Homo sapiens glutamate receptor. ionotropic, N-methyl D-aspartate 2A
Science 256:1217-1221(1992)
NCBI/NM 000833.2
             1          11         21         31         41         51
    1 MGRLGYWTLL VLPALLVWRD PAQNAAAEKG PPALNIAVLL GHSHDVTERE LRNLWGPEQA    60

61 TGLPLDVNVV ALLMNRTDPK SLITHVCDLM SGARIHGLVF GDDTDQEAVA QMLDFISSQT   120

121 FIPILGIHGG ASMIMADKDP TSTFFQFGAS IQQQATVMLK IMQDYDWHVF SLVTTIFPGY   180

181 RDFISFIKTT VDNSFVGWDM QNVITLDTSF EDAKTQVQLK KIHSSVILLY CSKDEAVLIL   240

241 SEARSLGLTG YDFFWIVPSL VSGNTELIPK EFPSGLISVS YDDWDYSLEA RVRDGLGILT   300

301 TAASSMLEKF SYIPEAKASC YGQAEKPETP LHTLHQFMVN VTWDGKDLSF TEEGYQVHPR   360

361 LVVIVLNKDR EWEKVGKWEN QTLSLRHAVW PRYKSFSDCE PDDNHLSIVT LEEAPFVIVE   420

421 DIDPLTETCV RNTVPCRKFV KINNSTNEGM NVKKCCKGFC IDILKKLSRT VKFTYDLYLV   480

481 TNGKHGKKVN NVWNGMIGEV VYQRAVMAVG SLTTINEERSE VVDFSVPFVE TGISVMVSRS   540

541 NGTVSPSAFL EPFSASVWVM MFVMLLIVSA IAVFVFEYFS PVGYNRNLAK GKAPHGPSFT   600

601 IGKAIWLLWG LVFNNSVPVQ NPKGTTSKIM VSVWAFFAVI FLASYTANLA AFMIQEEFVD   660

661 QVTGLSDKKF QRPHDYSPPF RFGTVPNGST ERNIRNNYPY MHQYMTRFNQ RGVEDALVSL   720

721 KTGKLDAFIY DAAVLNYKAG RDEGCKLVTI GSGYIFASTG YGIALQKGSP WKRQIDLALL   780

781 QFVGDGEMEE LETLWLTGIC HNEKNEVMSS QLDIDNMAGV FYMLAAAMAL SLITFIWEHL   840

841 FYWKLRFCFT GVCSDRPGLL FSISRGIYSC IHGVHIEEKK KSPDFNLTGS QSNMLKLLRS   900
```

```
-continued
 901 AKNISNMSNM NSSRMDSPKR ATDFIQRGSL IVDMVSDKGN LIYSDNRSFQ GKDSIFGDNM    960

961 NELQTFVANR HKDNLSNYVF QGQHPLTLNE SNPNTVEVAV STESKGNSRP RQLWKKSMES   1020

1021 LRQDSLNQNP VSQRDEKTAE NRTHSLKSPR YLPEEVAHSD ISETSSRATC HREPDNNKNH   1080

1081 KTKDNFKRSM ASKYPKDCSD VDRTYMKTKA SSPRDKIYTI DGEKEPSFHL DPPQFVENIT   1140

1141 LPENVGFPDT YQDHNENFRK GDSTLPMNRN PLHNEDGLPN NDQYKLYAKH FTLKDKGSPH   1200

1201 SEGSDRYRQN STHCRSCLSN LPTYSGHFTM RSPFKCDACL RMGNLYDIDE DQMLQETGNP   1260

1261 ATREEVYQQD WSQNNALQFQ KNKLRINRQH SYDNILDKPR EIDLSRPSRS ISLKDRERLL   1320

1321 EGNLYGSLFS VPSSKLLGNK SSLFPQGLED SKRSKSLLPD HASDNPFLHT YGDDQRLVIG   1380

1381 RCPSDPYKHS LPSQAVNDSY LRSSLRSTAS YCSRDSRGHS DVYISEHVMP YAANKNTMYS   1440

1441 TPRVLNSCSN RRVYKKMPSI ESDV
```

SEQ ID NO: 2. shows the amino acid sequence of the auto-antigenic region of the N-terminal domain of the NR2A subunit, as follows:

```
SEQ ID NO:2
HOMO SAPIENS
    PAQNAAAEKG PPALNIAVLL GHSHDVTERE LRNLWGPEQA                     60
 61 TGLPLDVNVV ALLMNRTDPK SLITHVCDLM SGARIHGLVF GDDTDQEAVA QMLDFISSQT 120
121 FIPILGIHGG ASMIMADKDP TSTFFQFGAS IQQQATVMLK IMQDYDWHVF SLVTTIFPGY 180
181 RDFISFIKTT VDNSFVGWDM QNVITLDTSF EDAKTQVQLK KIHSSVILLY CSKDEAVLIL 240
241 SEARSLGLTG YDFFWIVPSL VSGNTELIPK EFPSGLISVS YDDWDYSLEA RVRDGLGILT 300
301 TAASSMLEKF SYIPEAKASC YGQAEKPETP LHTLHQFMVN VTWDGKDLSF TEEGYQVHPR 360
361 LVVIVLNKDR EWEKVGKWEN QTLSLRHAVW PRYKSFSDCE PDDNHLSIVT LEEAPFVIVE 420
421 DIDPLTETCV RNTVPCRKFV KINNSTNEGM NVKKCCKGFC IDILKKLSRT VKFTYDLYLV 480
481 TNGKHGKKVN NVWNGMIGEV VYQRAVMAVG SLTINEERSE VVDFSVPFVE TGISVMVSRS 540
541 NGTVSPSAFL EPFSAS
```

SEQ ID NO: 3; shows a 21 amino acid antigenic peptide, corresponding to a fragment of the NR2A N-terminal domain another such peptide (21 amino acids derived from the NR2A sequence and an N-terminal Cys for attachment to a carrier protein), as follows:

```
SEQ ID NO:3
Homo sapiens
NGMIGEVVYQRAVMAVGSLTI
```

SEQ ID NO: 4. shows a 22 amino acid antigenic peptide, corresponding to a fragment of the NR2A N-terminal domain another such peptide, modified by an N-terminal Cys for attachment to a carrier protein):

Artificial Sequence

```
CNGMIGEVVYQRAVMAVGSLTI
```

Full

Base Count Origin

Homo sapiens glutamate receptor, ionotropic, N-methyl D-aspartate 2A (GRIN 2A) mRNA SEQ ID NO: 5. shows the Oligonucleotide position numbering used throughout in reference to NR2A oligonucleotide sequences, as follows:

SEQ ID NO:5
Science 256:1217-1221(1992)
May 22, 1992
NIGB/NM_000833

```
   1 atcatgggac cgggtgagcg ctgagaatcg cggccgcagc catcagccct ggagatgacc
  61 aggagcggcc actgctgaga actatgtgga gagaggctgc gagccctgct gcagagcctc
 121 cggctgggat agccgccccc cgtggggcg atgcggacag cgcgggacag ccaggggagc
 181 gcgctggggc cgcagcatgc gggaacccgc taaacccggt ggctgctgag gcggccgaga
 241 tgctcgtgcg cgcagcgcgc cccactgcat cctcgacctt ctcgggctac agggaccgtc
 301 agtggcgact atgggcagag tgggctattg accctgctg gtgctgccgg cccttctggt
 361 ctggcgcggt ccggcgccga gcgcggcggc ggagaagggt ccccccgcgc taaatattgc
 421 ggtgatgctg ggtcacagcc acgacgtgac agagcgcgaa cttcgaacac tgtggggccc
 481 cgagcaggcg gcggggctgc ccctggacgt gaacgtggta gctctgctga tgaaccgcac
 541 cgaccccaag agcctcatca cgcacgtgtg cgacctcatg tccggggcac gcatccacgg
 601 cctcgtgttt ggggacgaca cggaccagga ggccgtagcc cagatgctgg attttatctc
 661 ctcccacacc ttcgtcccca tcttgggcat tcatgggggc gcatctatga tcatggctga
 721 caaggatccg acgtctacct tcttccagtt tggagcgtcc atccagcagc aagccacggt
 781 catgctgaag atcatgcagg attatgactg gcatgtcttc ccctggtga ccactatctt
 841 ccctggctac agggaattca tcagcttcgt caagaccaca gtggacaaca gctttgtggg
 901 ctgggacatg cagaatgtga tcacactgga cacttccttt gaggatgcaa agacacaagt
 961 ccagctgaag aagatccact cttctgtcat cttgctctac tgttccaaag acgaggctgt
1021 tctcattctg agtgaggccc gctccctttgg cctcaccggg tatgatttct tctggattgt
1081 ccccagcttg gtctctggga acacggagct catcccaaaa gagtttccat cgggactcat
1141 ttctgtctcc tacgatgact gggactacag cctggaggcg agagtgaggg acggcattgg
1201 catcctaacc accgctgcat cttctatgct ggagaagttc tcctacatcc ccgaggccaa
1261 ggccagctgc tacgggcaga tggagaggcc agaggtcccg atgcacacct gcacccatt
1321 tatggtcaat gttacatggg atggcaaaga cttatccttc actgaggaag ctaccaggt
1381 gcaccccagg ctggtggtga ttgtgctgaa caaagaccgg gaatgggaaa aggtgggcaa
1441 gtgggagaac catacgctga gcctgaggca cgccgtgtgg cccaggtaca agtccttctc
1501 cgactgtgag ccggatgaca accatctcag catcgtcacc ctggaggagg ccccattcgt
1561 catcgtggaa gacatagacc ccctgaccga gacgtgtgtg aggaacaccg tgccatgtcg
1621 gaagttcgtc aaaatcaaca attcaaccaa tgagggatg aatgtgaaga atgctgcaa
1681 ggggttctgc attgatattc tgaagaagct ttccagaact gtgaagttta cttacgacct
1741 ctatctggtg accaatggga agcatggcaa gaaagttaac aatgtgtgga atggaatgat
1801 cggtgaagtg gtctatcaac gggcagtcat ggcagttggc tcgctcacca tcaatgagga
1861 acgttctgaa gtggtggact ctctctgtgcc ctttgtggaa acgggaatca gtgtcatggt
1921 ttcaagaagt aatggcaccg tctcaccttc tgcttttcta gaaccattca gcgcctctgt
1981 ctgggtgatg atgtttgtga tgctgctcat tgtttctgcc atagctgttt ttgtctttga
2041 atacttcagc cctgttggat acaacagaaa cttagccaaa gggaaagcac ccatgggcc
2101 ttcttttaca attggaaaag ctatatggct tctttgggc ctggtgttca ataactccgt
2161 gcctgtccag aatcctaaag ggaccaccag caagatcatg gtatctgtat gggccttctt
2221 cgctgtcata ttcctggcta gctacacagc caatctggct gccttcatga tccaagagga
```

-continued

```
2281 atttgtggac caagtgaccg gcctcagtga caaaaagttt cagagacctc atgactattc
2341 cccacctttt cgatttggga cagtgcctaa tggaagcacg gagagaaaca ttcggaataa
2401 ctatccctac atgcatcagt acatgaccaa atttaatcag aaaggagtag aggacgcctt
2461 ggtcagcctg aaaacgggga agctggacgc tttcatctac gatgccgcag tcttgaatta
2521 caaggctggg agggatgaag ctgcaagct ggtgaccatc gggagtgggt acatctttgc
2581 caccaccggt tatggaattg cccttcagaa aggctctcct tggaagaggc agatcgacct
2641 ggccttgctt cagtttgtgg gtgatggtga gatggaggag ctggagaccc tgtggctcac
2701 tgggatctgc cacaacgaga agaacgaggt gatgagcagc cagctggaca ttgacaacat
2761 ggcgggcgta ttctacatgc tggctgccgc catggccctt agcctcatca ccttcatctg
2821 ggagcacctc ttctactgga agctgcgctt ctgtttcacg ggcgtgtgct ccgaccggcc
2881 tgggttgctc ttctccatca gcaggggcat ctacagctgc attcatggag tgcacattga
2941 agaaaagaag aagtctccag acttcaatct gacgggatcc cagagcaaca tgttaaaact
3001 cctccggtca gccaaaaaca tttccagcat gtccaacatg aactcctcaa gaatggactc
3061 acccaaaaga gctgctgact tcatccaaag aggttccctc atcatggaca tggtttcaga
3121 taagggggaat ttgatgtact cagacaacag gtcctttcag gggaagagaa gcatttttgg
3181 agacaacatg aacgaactcc aaacatttgt ggccaaccgg cagaaggata acctcaataa
3241 ctatgtattc cagggacaac atcctcttac tctcaatgag tccaacccta acacggtgga
3301 ggtggccgtg agcacagaat ccaaagcgaa ctctagaccc cggcagctgt ggaagaaatc
3361 cgtggattcc atacgccagg attcactatc ccagaatcca gtctcccaga gggatgaggc
3421 aacagcagag aataggaccc actccctaaa gagccctagg tatcttccag aagagatggc
3481 ccactctgac atttcagaaa cgtcaaatcg ggccacgtgc cacagggaac ctgacaacag
3541 taagaaccac aaaaccaagg acaactttaa aaggtcagtg gcctccaaat accccaagga
3601 ctgtagtgag gtcgagcgca cctacctgaa aaccaaatca agctcccta gagacaagat
3661 ctacactata gatggtgaga aggagcctgg tttccactta gatccacccc agtttgttga
3721 aaatgtgacc ctgcccgaga acgtggactt cccggacccc taccaggatc ccagtgaaaa
3781 cttccgcaag ggggactcca cgctgccaat gaaccggaac cccttgcata tgaagagggg
3841 gctttccaac aacgaccagt ataaactcta ctccaagcac ttcaccttga agacaagggg
3901 ttccccgcac agtgagacca gcgagcgata ccggcagaac tccacgcact gcagaagctg
3961 cctttccaac atgcccacct attcaggcca cttcaccatg aggtccccct tcaagtgcga
4021 tgcctgcctg cggatgggga acctctatga catcgatgaa gaccagatgc ttcaggagac
4081 aggtaaccca gccaccgggg agcaggtcta ccagcaggac tgggcacaga caatgcccct
4141 tcaattacaa aagaacaagc taaggattag ccgtcagcat tcctacgata acattgtcga
4201 caaacctagg gagctagacc ttagcaggcc ctcccggagc ataagcctca aggacaggga
4261 acggcttctg gagggaaatt tttacggcag cctgtttagt gtcccctcaa gcaaactctc
4321 ggggaaaaaa agctccccttt tcccccaagg tctggaggac agcaagagga gcaagtctct
4381 cttgccagac cacacctccg ataacccttt cctccactcc cacagggatg accaacgctt
4441 ggttattggg agatgcccct cggacccctta caaacactcg ttgccatccc aggcggtgaa
4501 tgacagctat cttcggtcgt ccttgaggtc aacggcatcg tactgttcca gggacagtcg
4561 gggccacaat gatgtgtata tttcggagca tgttatgcct tatgctgcaa ataagaataa
4621 tatgtactct accccaggg ttttaaattc ctgcagcaat agacgcgtgt acaagaaaat
```

```
                            -continued
4681 gcctagtatc gaatctgatg tttaaaaatc ttccattaat gttttatcta tagggaaata 4741 cacgtaatgg ccaatgttct ggagggtaaa tgttggatgt ccaatagtgc cctgctaaga 4801 ggaagaagat gtagggaggt attttgttgt tgttgttgtt ggctcttttg cacacggctt 4861 catgccataa tcttccactc aaggaatctt gtgaggtgtg tgctgagcat ggcagacacc 4921 agataggtga gtccttaacc aaaaataact aactacataa gggcaagtct ccgggacatg 4981 cctactgggt atgttggcaa taatgatgca ttggatgcca atggtgatgt tatgatttcc 5041 tatattccaa attccattaa ggtcagccca ccatgtaatt ttctcatcag aaatgcctaa 5101 tggtttctct aatacagaat aagcaatatg gtgtgcatgt aaacctgaca cagacaaaat 5161 aaaaacagtt aagaatgcat ctgcactgta gtcggatttg aacatgtgca agagattagg 5221 aagtttggct cgtaacagtt tcagctttct tgttatgcct tccatcacag cccaggctca 5281 ccccaagaac tccaggctcc cctaaagaat agcaaatcag tgtgttcgtg atgactgtgc 5341 taccttcatt atagttcatt tccaagacac atctggagcc aaaggcccga gggaccctca 5401 ggtggggaga gctacaggaa tctctttgga tgttgatgtg tgtttctctc taccctcggc 5461 ttcgatggtc ttgttcagag ctgcataaac taacacattt atgtctccga gatctaagtg 5521 tggatcttct gtctgtgaca cagtggccat tgtagtttat cccgaagacg cctatgtacg 5581 taagtttgca tttcctccct tctggtgatg actcagggtt gtatagtatc tgttacccct 5641 tccctcccag agtaaccata actcgttccg tttccaaaca gccatggtgg tgtccaatta 5701 gctgtgtatc gctcttccca gagttgttaa tgtggtgaca tgcaccaaca gccgtatgtg 5761 tactgtgatc tgtaagaagt acaatgccat ctgtctgccg aaggctagca tggttttagg 5821 tttatcttcc ttcacatcca gaaattctgt tggacactca cttccacccc aaactcctca 5881 aatcaaaagc cttcaaaaca cgaggcactc ttggatctac cctgagtatc ctccaaactg 5941 tggatacagt ttagtgagac aagcaatttc tcccttctga gttattctct ctgttggtgg 6001 caaaccactt catagcacca acagagatgt aggaaaaatt cctcaaagta tttgtcattt 6061 ctgagtcgcc tgcattatcc cattcttatt ctcctoaaac ctgtgcatat atgacatgaa 6121 atgatatcca ttttttttt aagttagaaa cagagagggg aatacttatg catggggagc 6181 ctgttagcac agtgcctgcc acaaaaacaa gtgcccccga caagatagtt gctatgttat 6241 gacactttct cagatcagga ttttctagtt taaaaattaa atatcataaa acg
```

SEQ ID NO: 6. shows the oligonucleotide sequence of the auto-antigenic region of the N-terminal domain of the NR2A subunit, as follows:

```
SEQ ID NO:6
N-terminal nucleotide sequence
 371 ccggcgccga gcgcggcggc ggagaagggt ccccccgcgc taaatattgc 421 ggtgatgctg ggtcacagcc acgacgtgac agagcgcgaa cttcgaacac tgtggggccc 481 cgagcaggcg gcggggctgc ccctggacgt gaacgtggta gctctgctga tgaaccgcac 541 cgaccccaag agcctcatca cgcacgtgtg cgacctcatg tccggggcac gcatccacgg 601 cctcgtgttt ggggacgaca cggaccagga ggccgtagcc cagatgctgg attttatctc 661 ctcccacacc ttcgtcccca tcttgggcat tcatggggc gcatctatga tcatggctga 721 caaggatccg acgtctacct tcttccagtt tggagcgtcc atccagcagc aagccacggt 781 catgctgaag atcatgcagg attatgactg gcatgtcttc tccctggtga ccactatctt
```

-continued

```
 841 ccctggctac agggaattca tcagcttcgt caagaccaca gtggacaaca gctttgtggg
 901 ctgggacatg cagaatgtga tcacactgga cacttccttt gaggatgcaa agacacaagt
 961 ccagctgaag aagatccact cttctgtcat cttgctctac tgttccaaag acgaggctgt
1021 tctcattctg agtgaggccc gctcccttgg cctcaccggg tatgatttct tctggattgt
1081 ccccagcttg gtctctggga cacggagct catcccaaaa gagtttccat cgggactcat
1141 ttctgtctcc tacgatgact gggactacag cctggaggcg agagtgaggg acggcattgg
1201 catcctaacc accgctgcat cttctatgct ggagaagttc tcctacatcc ccgaggccaa
1261 ggccagctgc tacgggcaga tggagaggcc agaggtcccg atgcacacct tgcacccatt
1321 tatggtcaat gttacatggg atggcaaaga cttatccttc actgaggaag gctaccaggt
1381 gcaccccagg ctggtggtga ttgtgctgaa caaagaccgg gaatgggaaa aggtgggcaa
1441 gtgggagaac catacgctga gcctgaggca cgccgtgtgg cccaggtaca agtccttctc
1501 cgactgtgag ccggatgaca accatctcag catcgtcacc ctggaggagg ccccattcgt
1561 catcgtggaa gacatagacc ccctgaccga gacgtgtgtg aggaacaccg tgccatgtcg
1621 gaagttcgtc aaaatcaaca attcaaccaa tgaggggatg aatgtgaaga atgctgcaa
1681 ggggttctgc attgatattc tgaagaagct ttccagaact gtgaagttta cttacgacct
1741 ctatctggtg accaatggga agcatggcaa gaaagtttaac aatgtgtgga atggaatgat
1801 cggtgaagtg gtctatcaac gggcagtcat ggcagttggc tcgctcacca tc aatgagga
1861 acgttctgaa gtggtggact ctctctgtgcc ctttgtggaa acgggaatca gtgtcatggt
1921 ttcaagaagt aatggcaccg tctcaccttc tgcttttcta gaaccattca gcgcctct
```

SEQ ID NO: 7 shows a 62 oligonucleotide fragment target, as follows:

SEQ ID NO:7
atggaatgatcggtgaagtggtctatcaacgggcagtcatggcagttggc
tcgctcaccatc

SEQ ID NO: 8 shows one oligonucleotide primer, as follows:

SEQ ID NO:8
agcatggcaagaaagttaaca

SEQ ID NO: 9 shows a second oligonucleotide primer, as follows:

SEQ ID NO:9
acgttctgaagtggtggactt

SEQ ID NO: 10. shows the full-length amino acid sequence of the mature NR2B receptor subunit, as follows:

```
PEPTIDE
Homo sapiens glutamate receptor, Ionotropic, N-methyl D-aspartate 2B
Biochim. Biophys. Acta 1260:105-108(1995).
sequence NME2_HUMAN (Q13224)
            1         11         21         31         41         51
   1 MKPRAECCSP KFWLVLAVLA VSGSRARSQK SPPSIGIAVI LVGTSDEVAI KDAHEKDDFH   60

61 HLSVVPRVEL VAMNETDPKS IITRICDLMS DRKIQGVVFA DDTDQEAIAQ ILDFISAQTL  120

121 TPILGIHGGS SMIMADKDES SMFFQFGPSI EQQASVMLNI MEEYDWYIFS IVTTYFPGYQ  180

181 DFVNKIRSTI ENSFVGWELE EVLLLDMSLD DGDSKIQNQL KKLQSPIILL YCTKEEATYI  240

241 FEVANSVGLT GYGYTWIVPS LVAGDTDTVP AEFPTGLISV SYDEWDYGLP ARVRDGIAII  300

301 TTAASDMLSE HSFIPEPKSS CYNTHEKRIY QSNMLNRYLI NVTFEGRNLS FSEDGYQMHP  360

361 KLVIILLNKE RKWERVGKWK DKSLQMKYYV WPRMCPETEE QEDDHLSIVT LEEAPFVIVE  420

421 SVDPLSGTCM RNTVPCQKRI VTENKTDEEP GYIKKCCKGF CIDILKKISK SVKFTYDLYL  480
```

```
481 VTNGKHGKKI NGTWNGMIGE VVMKRAYMAV GSLTINEERS EVVDFSVPFI ETGISVMVSR    540

541 SNGTVSPSAF LEPFSADVWV MMFVMLLIVS AVAVFVFEYF SPVGYNRCLA DGREPGGPSF    600

601 TIGKAIWLLW GLVFNNSVPV QNPKGTTSKI MVSVWAFFAV IFLASYTANL AAFMIQEEYV    660

661 DQVSGLSDKK FQRPNDFSPP FRFGTVPNGS TERNIRNNYA EMHAYMGKFN QRGVDDALLS    720

721 LKTGKLDAFI YDAAVLNYMA GRDEGCKLVT IGSGKVFAST GYGIAIQKDS GWKRQVDLAI    780

781 LQLFGDGEME ELEALWLTGI CHNEKNEVMS SQLDIDNMAG VFYMLGAAMA LSLITFICEH    840

841 LFYWQFRHCF MGVCSGKPGM VFSISRGIYS CIHGVAIEER QSVMNSPTAT MNNTHSNILR    900

901 LLRTAKNMAN LSGVNGSPQS ALDFIRRESS VYDISEHRRS FTHSDCKSYN NPPCEENLFS    960

961 DYISEVERTF GNLQLKDSNV YQDHYHHHHR PHSIGSASSI DGLYDCDNPP FTTQSRSISK   1020

1021 KPLDIGLPSS KHSQLSDLYG KFSFKSDRYS GHDDLIRSDV SDISTHTVTY GNIEGNAAKR   1080

1081 RKQQYKDSLK KRPASAKSRR EFDEIELAYR RRPPRSPDHK RYFRDKEGLR DFYLDQFRTK   1140

1141 ENSPHWEHVD LTDIYKERSD DFKRDSVSGG GPCTNRSHIK HGTGDKHGVV SGVPAPWEKN   1200

1201 LTNVEWEDRS GGNFCRSCPS KLHNYSTTVT GQNSGRQACI RCEACKKAGN LYDISEDNSL   1260

1261 QELDQPAAPV AVTSNASTTK YPQSPTNSKA QKKNRNKLRR QHSYDTFVDL QKEEAALAPR   1320

1321 SVSLKDKGRF MDGSPYAHMF EMSAGESTFA NNKSSVPTAG HHHHNNPGGG YMLSKSLYPD   1380

1381 RVTQNPFIPT FGDDQCLLHG SKSYFFRQPT VAGASKARPD FRALVTNKPV VSALHGAVPA   1440

1441 RFQKDICIGN QSNPCVPNNK NPRAFNGSSN GHVYEKLSSI
```

SEQ ID NO: 11. shows the amino acid sequence of the auto-antigenic region of the N-terminal domain of the NR2B subunit, as follows:

```
SEQ ID NO:11
Homo sapiens
     RSQK SPPSIGIAVI LVGTSDEVAI KDAHEKDDFH                              60

61 HLSVVPRVEL VAMNETDPKS IITRICDLMS DRKIQGVVFA DDTDQEAIAQ ILDFISAQTL 120

121 TPILGIHGGS SMIMADKDES SMFFQFGPSI EQQASVMLNI MEEYDWYIFS IYTTYFPGYQ 180

181 DFVNKIRSTI ENSFVGWELE EVLLLDMSLD DGDSKIQNQL KKLQSPIILL YCTKEEATYI 240

241 FEVANSVGLT GYGYTWIVPS LVAGDTDTVP AEFPTGLISV SYDEWDYGLP ARVRDGIAII 300

301 TTAASDMLSE HSFIPEPKSS CYNTHEKRIY QSNMLNRYLI NVTFEGRNLS FSEDGYQMHP 360

361 KLVIILLNKE RKWERVGKWK DKSLQMKYYV WPRMGPETEE QEDDHLSIVT LEEAPFVIVE 420

421 SVDPLSGTCM RNTVPCQKRI VTENKTDEEP GYIKKCCKGF CIDILKKISK SVKFTYDLYL 480

481 VTNGKHGKKI NGTWNGMIGE VVMKRAYMAV GSLTINEERS EVVDFSVPFI ETGISVMVSR 540

541 SNGTVSPSAF LEPFSAD
```

SEQ ID NO: 12; shows a 20 amino acid antigenic peptide fragment of the NR2B subunit, as follows:

```
SEQ ID NO:12
Homo sapiens
GYIKKCCKGF CIDILKKISK
```

SEQ ID NO: 13 shows a 21 amino acid sequence of an antigenic fragment of the NR2B subunit modified by an N-terminal Cys for attachment to a carrier protein, as follows:

```
SEQ ID NO:13
Artificial Sequence (21 aminoacids)
CGYIKKCCKGF CIDILKKISK.
```

Full

Base Count Origin

SEQ ID NO: 14 shows the oligonucleotide position numbering used throughout in reference to NR2B oligonucleotide sequences, as follows:

SEQ. NO. 14
Homo sapiens glutamate receptor, ionotropic, N-methyl D-aspartate
2B mRNA

```
   1 ttgaatttgc atctcttcaa gacacaagat taaaacaaaa tttacgctaa attggatttt
  61 aaattatctt ccgttcattt atccttcgtc tttcttatgt ggatatgcaa gcgagaagaa
 121 gggactggac attcccaaca tgctcactcc cttaatctgt ccgtctagag gtttggcttc
 181 tacaaaccaa gggagtcgac gagttgaaga tgaagcccag agcggagtgc tgttctccca
 241 agttctggtt ggtgttggcc gtcctggccg tgtcaggcag cagagctcgt tctcagaaga
 301 gccccccccag cattggcatt gctgtcatcc tcgtgggcac ttccgacgag gtggccatca
 361 aggatgccca cgagaaagat gatttccacc atctctccgt ggtacccccgg gtggaactgg
 421 tagccatgaa tgagaccgac ccaaagagca tcatcacccg catctgtgat ctcatgtctg
 481 accggaagat ccaggggggtg gtgtttgctg atgacacaga ccaggaagcc atcgcccaga
 541 tcctcgattt catttcagca cagactctca ccccgatcct gggcatccac gggggctcct
 601 ctatgataat ggcagataag gatgaatcct ccatgttctt ccagtttggc ccatcaattg
 661 aacagcaagc ttccgtaatg ctcaacatca tggaagaata tgactggtac atcttttcta
 721 tcgtcaccac ctatttccct ggctaccagg actttgtaaa caagatccgc agcaccattg
 781 agaatagctt tgtgggctgg agctagagg aggtcctcct actggacatg tccctggacg
 841 atggagattc taagatccag aatcagctca agaaacttca aagccccatc attcttcttt
 901 actgtaccaa ggaagaagcc acctacatct ttgaagtggc caactcagta gggctgactg
 961 gctatggcta cacgtggatc gtgcccagtc tggtggcagg ggatacagac acagtgcctg
1021 cggagttccc cactgggctc atctctgtat catatgatga atgggactat ggcctccccg
1081 ccagagtgag agatggaatt gccataatca ccactgctgc ttctgacatg ctgtctgagc
1141 acagcttcat ccctgagccc aaaagcagtt gttacaacac ccacgagaag agaatctacc
1201 agtccaatat gctaaatagg tatctgatca atgtcacttt tgagggggag aatttgtcct
1261 tcagtgaaga tggctaccag atgcacccga aactggtgat aattcttctg aacaaggaga
1321 ggaagtggga aagggtgggg aagtggaaag acaagtccct gcagatgaag tactatgtgt
1381 ggccccgaat gtgtccagag actgaagagc aggaggatga ccatctgagc attgtgaccc
1441 tggaggaggc ccatttgtc attgtggaaa gtgtggaccc tctgagtgga acctgcatga
1501 ggaacacagt ccccctgcca aaaacgcatag tcactgagaa taaaacagac gaggagccgg
1561 gttacatcaa aaaatgctgc aagggggttct gtattgacat ccttaagaaa atttctaaat
1621 ctgtgaagtt cacctatgac ctttacctgg ttaccaatgg caagcatggg aagaaaatca
1681 atggaacctg gaatggtatg attggagagg tggtcatgaa gagggcctac atggcagtgg
1741 gctcactcac catcaatgag gaacgatcgg aggtggtcga cttctctgtg cccttcatag
1801 agacaggcat cagtgtcatg gtgtcacgca gcaatgggac tgtctcacct tctgccttct
1861 tagagccatt cagcgctgac gtatgggtga tgtgtttgt gatgctgctc atcgtctcag
1921 ccgtggctgt ctttgtcttt gagtacttca gccctgtggg ttataacagg tgcctcgctg
1981 atggcagaga gcctggtgga ccctctttca ccatcggcaa agctatttgg ttgctctggg
2041 gtctggtgtt taacaactcc gtacctgtgc agaacccaaa ggggaccacc tccaagatca
2101 tggtgtcagt gtgggccttc tttgctgtca tcttcctggc cagctacact gccaacttag
2161 ctgccttcat gatccaagag gaatatgtgg accaggtttc tggcctgagc gacaaaaagt
2221 tccagagacc taatgacttc tcaccccctt tccgctttgg gaccgtgccc aacggcagca
2281 cagagagaaa tattcgcaat aactatgcag aaatgcatgc ctacatggga aagttcaacc
```

-continued

```
2341 agagggtgt agatgatgca ttgctctccc tgaaaacagg gaaactggat gccttcatct
2401 atgatgcagc agtgctgaac tatatggcag gcagagatga aggctgcaag ctggtgacca
2461 ttggcagtgg gaaggtcttt gcttccactg gctatggcat tgccatccaa aaagattctg
2521 ggtggaagcg ccaggtggac cttgctatcc tgcagctctt tggagatggg gagatggaag
2581 aactggaagc tctctggctc actggcattt gtcacaatga agaatgag gtcatgagca
2641 gccagctgga cattgacaac atggcagggg tcttctacat gttggggcg gccatggctc
2701 tcagcctcat caccttcatc tgcgaacacc ttttctattg gcagttccga cattgcttta
2761 tgggtgtctg ttctggcaag cctggcatgg tcttctccat cagcagaggt atctacagct
2821 gcatccatgg ggtggcgatc gaggagcgcc agtctgtaat gaactccccc accgcaacca
2881 tgaacaacac acactccaac atcctgcgcc tgctgcgcac ggccaagaac atggctaacc
2941 tgtctggtgt gaatggctca ccgcagagcg ccctggactt catccgacgg gagtcatccg
3001 tctatgacat ctcagagcac cgccgcagct tcacgcattc tgactgcaaa tcctacaaca
3061 acccgccctg tgaggagaac ctcttcagtg actacatcag tgaggtagag agaacgttcg
3121 ggaacctgca gctgaaggac agcaacgtgt accaagatca ctaccaccat caccaccggc
3181 cccatagtat tggcagtgcc agctccatcg atgggctcta cgactgtgac aacccaccct
3241 tcaccaccca gtccaggtcc atcagcaaga agccctgga catcggcctc ccctcctcca
3301 agcacagcca gctcagtgac ctgtacggca aattctcctt caagagcgac cgctacagtg
3361 gccacgacga cttgatccgc tccgatgtct ctgacatctc aacccacacc gtcacctatg
3421 ggaacatcga gggcaatgcc gccaagaggc gtaagcagca atataaggac agcctgaaga
3481 agcggcctgc ctcggccaag tcccgcaggg agtttgacga gatcgagctg gcctaccgtc
3541 gccgaccgcc ccgctcccct gaccacaagc gctacttcag ggacaaggaa gggctacggg
3601 acttctacct ggaccagttc cgaacaaagg agaactcacc ccactgggag cacgtagacc
3661 tgaccgacat ctacaaggag cggagtgatg actttaagcg cgactccatc agcggaggag
3721 ggccctgtac caacaggtct cacatcaagc acgggacggg cgacaaacac ggcgtggtca
3781 gcggggtacc tgcaccttgg gagaagaacc tgaccaacgt ggagtgggag gaccggtccg
3841 ggggcaactt ctgccgcagc tgtccctcca agctgcacaa ctactccacg acggtgacgg
3901 gtcagaactc gggcaggcag gcgtgcatcc ggtgtgaggc ttgcaagaaa gcaggcaacc
3961 tgtatgacat cagtgaggac aactccctgc aggaactgga ccagccggct gccccagtgg
4021 cggtgacgtc aaacgcctcc accactaagt accctcagag cccgactaat tccaaggccc
4081 agaagaagaa ccggaacaaa ctgcgccggc agcactccta cgacaccttc gtggacctgc
4141 agaaggaaga agccgccctg gccccgcgca gcgtaagcct gaaagacaag ggccgattca
4201 tggatgggag ccctacgcc cacatgtttg agatgtcagc tggcgagagc acctttgcca
4261 acaacaagtc ctcagtgccc actgccggac atcaccacca caacaacccc ggcggcgggt
4321 acatgctcag caagtcgctc taccctgacc gggtcacgca aaacccttc atccccactt
4381 ttgggacga ccagtgcttg ctccatggca gcaaatccta cttcttcagg cagcccacgg
4441 tggcggggc gtcgaaagcc aggccggact ccgggccct tgtcaccaac aagccggtgg
4501 tctcggccct tcatggggcc gtgccagccc gtttccagaa ggacatctgt atagggaacc
4561 agtccaaccc ctgtgtgcct aacaacaaaa accccagggc tttcaatggc tccagcaatg
4621 ggcatgttta tgagaaactt tctagtattg agtctgatgt ctgagtgagg gaacagagag
4681 gttaaggtgg gtacgggagg gtaaggctgt gggtcgcgtg atgcgcatgt cacggagggt
```

-continued

```
4741 gacggggtg aacttggttc ccatttgctc ctttcttgtt ttaatttatt tatgggatcc
4801 tggagttctg gttcctactg ggggcaaccc tggtgaccag caccatctct cctccttttc
4861 acagttctct ccttcttccc cccgctgtca gccattcctg ttcccatgag atgatgccat
4921 gggccctctc agcaggggag ggtagagcgg agaaaggaag ggctgcatgc gggcttcctc
4981 ctggtgtgga agagctcctt gatatcctct ttgagtgaag ctgggagaac caaaaagagg
5041 ctatgtgagc acaaaggtag cttttcccaa actgatcttt tcatttaggt gaggaagcaa
5101 aagcatctat gtgagaccat ttagcacact gcttgtgaaa ggaaagaggc tctggctaaa
5161 ttcatgctgc ttagatgaca tctgtctagg aatcatgtgc caagcagagg ttgggaggcc
5221 atttgtgttt atatataagc ccaaaaatgc ttgcttcaac cccatgagac tcgatagtgg
5281 tggtgaacag aacccaaggt cattggtggc agagtggatt cttgaacaaa ctggaaagta
5341 cgttatgata gtgtcccccg gtgccttggg gacaagagca ggtggattgt gcgtgcatgt
5401 gtgttcatgc acacttgcac ccatgtgtag tcaggtgcct caagagaagg caaccttgac
5461 tctttctatt gtttctttca atatccccaa gcagtgtgat tgtttggctt atatacagac
5521 agagatggcc atgtattacc tgaattttgg ctgtgtctcc cttcatcctt ctggaataag
5581 gagaatgaaa attcttgata aagaagattc tgtggtctaa acaaaaaaag gcggtgagca
5641 atcctgcaag aacaaggtac ataaacaagt cctcagtggt tggcaattgt ttcaaccagt
5701 ttgaaccaag aactttccag gaaggctaaa gggaaaccga attttcacag ccatgattct
5761 tttgcccaca cttgggagca aaagattcta caaagctctt ttgagcattt agactctcga
5821 ctggccaagg tttggggaag aacgaagcca cctttgaaga agtaaggagt cgtgtatggt
5881 agggtaagtg agagaggggg atgtttccaa tgctttgatc ccttcttact taacctgaag
5941 ctagacgagc aggcttcttc cccccaaaac tgattacaac tgctacagag cagacagtta
6001 agagaaatga gcttgacctt taagagaaat gagctgcact ccatgagtgc agctctggag
6061 gtacgaaaag aggggaagag acttggaaat gggagacggg ggcagagagg gaccctccac
6121 cacctctttg ggcctggctc cctgggaatg tgacttgagc ccagagtgaa cactcttggt
6181 agaagcccctt ctaccttcct gcaacacctt gtttccctct cagattgtac cattgag
```

SEQ ID NO: 15 shows a 60 oligonucleotide fragment target, as follows:

```
SEQ ID NO:15
g gttacatcaa aaaatgctgc aagggttct gtattgacat ccttaagaaa atttctaaa
```

SEQ ID NO: 16 shows one oligonucleotide primers (21 nucleotides), as follows:

```
SEQ ID NO:16
tcactgagaa taaaacagac g
```

SEQ ID NO: 17 shows one oligonucleotide primers (21 nucleotides), as follows:

```
SEQ ID NO:17
t cacctatgac ctttacctgg
```

EXAMPLES

The following examples are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at room temperature, and pressure is at or near atmospheric.

Example 1

Preparation of Polyclonal Antibodies (IGG) to Glutamate and Homocysteine

Glutamate (polyglutamate, 10 amino acids) or homocysteine (polyhomocysteine, 10 amino acids) alone will not generate antibodies when injected into an animal. Therefore, polyglutamate and polyhomocysteine were conjugated with human serum albumin for the immunization to obtain polyclonal antibodies. For glutaraldehyde conjugation, polyglutamate or homocysteine (10 mg) and 40 mg bovine serum albumin (BSA, Sigma, St. Louis, Mo.) were incubated for 2 hr at room temperature in 4 ml of PBS containing 5% glutaraldehyde. The reaction was stopped by adding glycine to a final concentration of 0.2 M, and the conjugate was dialyzed against PBS.

Rabbits were given initial injections of 1 mg of conjugated glutamate (polyglutamate) or homocysteine (polyhomocysteine) in complete Freund's and subsequent increased doses of injections (2 mg) in incomplete Freund's adjuvant at successive 2 week intervals. All injections were given subcutaneously. The immunization period lasted for 110 days. Antibodies (IgG) were affinity purified according to standard procedures (Warr, G. W., Purification of antibodies, In: Antibody as a Tool, Eds., Marchalonis, J. J., and G. W. Warr, J. Wiley, UK, pp. 59-96 (1982)) and were shown to be selective for glutamate or homocysteine by ELISA assay.

Example 2

Preparation of Polyclonal Antibodies (IGG) to NR2A Receptor Peptide

Using computer analysis of the hydrophobicity profile of human NR2A and NR2B NMDA receptors to predict the antigenic determinants in the protein structure, we selected fragments corresponding to the N-terminal sequence of human NR2A and NR2B receptor peptides for synthesis. The fragments corresponded to the N-terminal sequence of the NR2A and NR2B receptors, represented by SEQ ID NO: 1 and SEQ ID NO: 2 for the NR2A and NR2B receptors, respectively. The peptide fragments were reproduced using solid-phase synthesis, and had a purity ranging from 90% to 98%. The peptide sequences were verified by amino acid analysis after acid hydrolysis. A mixture of NR2A and NR2B peptides (1:1) was conjugated with human serum albumin for the immunization to obtain polyclonal antibodies. For glutaraldehyde conjugation, 10 mg of the mixture of peptides and 40 mg human serum albumin (Sigma, St. Louis, Mo.) were incubated for 1.45 hr at room temperature in 4 ml of PBS containing 5% glutaraldehyde. The reaction was stopped by adding glycine to a final concentration of 0.2 M, and the conjugate was dialyzed against PBS.

Rabbit polyclonal antibodies were raised against the NR2A-B peptides. Rabbits were given initial injections of 1 mg of conjugated peptides in complete Freund's adjuvant and subsequent injections (0.5 mg) in incomplete Freund's adjuvant at successive 2 week intervals. Antibodies were affinity purified according to standard procedures (Warr, G. W., Purification of antibodies, In: Antibody as a Tool, Eds., Marchalonis, J. J., and G. W. Warr, J. Wiley, UK, pp. 59-96 (1982)) and were shown to be selective for NR2A and NR2B NMDA receptors using an ELISA assay.

Example 3

Preparation of Latex Beads Containing Biomarker Antibodies

Three different sensitized latex beads containing IgG against glutamate, homocysteine and NR2A-B receptor peptides were prepared using two types of blue polystyrene latex beads (diameter, 0.25 and 0.4 µM; Sigma, St. Louis, Mo.) as follows. A 1% suspension of latex beads in 50 mM PBS (1 ml, pH 7.0) was mixed with an equal volume of corresponding IgG (2 mg/ml) and incubated on a shaker at room temperature for 2 hours. The mixture was then washed twice with PBS by centrifugation at 9,500 g for 5 min. The pellet was suspended in PBS containing 1% BSA overnight at 4° C. After being washed twice with PBS, the sensitized latex beads were resuspended in latex diluent (50 mM PBS with 1% BSA) at a concentration of 0.4% and stored at 4° C. until used.

Preliminary experiments with latex agglutination (LA) alone were performed to identify problems and to select the most desirable latex particle size. Two types of commercial latex beads were coated with antibodies at various concentrations. Tests were initially performed with the corresponding amino acid or NR2A and NR2B receptor peptides as controls. Particle size and IgG concentration were found to be the primary factors affect the sensitivity of the test. The most desirable particle size was found to be 0.25 µm (blue latex) because particles of this size agglutinated each amino acid and peptide specifically. Higher IgG concentrations showed higher sensitivities. Using blue latex bead coated with 2 mg of IgG per ml, agglutination could be observed within 30 min.

Example 4

Latex Agglutination Analysis of Blood Serum Specimens

Blood samples (5 ml) were collected using standard venipuncture clinical protocol, from patients with TIA, stroke and brain injury (n=30) and examined at the laboratory of CIS Biotech, Inc. in Atlanta (Ga., USA). None of the patients had been treated with anticoagulants, and serum samples were obtained from the clotted blood. All specimens were free of visible lipids, white blood cells, platelets, fibrin, mucus or other contaminants that could cause "false positive" reactions. Platelets, white blood cells, mucus and fibrin were removed by centrifugation. Lipids were removed by filtration.

Specimens to be tested within 72 hours after collection were stored at 2-8° C. For longer storage periods, −20° C. or colder is recommended.

The semi-quantitative analysis of glutamate, homocysteine and NR2A-B receptor peptides in the serum samples is basically a three step process: serum sample dilution, reaction of latex beads with serum samples, and product analysis.

In previous experiments serial dilutions of the serum samples from 1:4 to 1:64 in saline containing 4% glycerol for better agglutination were performed. The highest dilution in which agglutination was observed corresponded to the sample titer.

Two 25 µl aliquots of coated latex beads containing the corresponding IgG were layered on a double-concave slide (Fisher Sci., Norcross, Ga.), one with 25 µl of the serum sample in serial dilution to be tested and one with 25 µl of PBS as a negative control. After gentle mixing with vortex, agglutination was judged macroscopically against a dark background. A negative reaction corresponded to a homogeneous lactescent background with no agglutination; a positive reaction corresponded to a clearly visible agglutination against the black background and weakly visible agglutination on a slightly lactescent background.

The highest dilution at which agglutination occurs gives the titer of the sample. To obtain the approximate titer in µg/ml we used the following calculation:

$$\text{Titer } \mu g/ml = A \times D$$

where A is the test sensitivity, and D is the highest dilution at which agglutination occurs.

Example 5

Description of Patients

Patients observed in trials (n=68) included 9 with pre-stroke, 9 with TIA (mean age 52.0±3.0), 31 with acute ischemic stroke (mean age 54.7±1.4) and 11 with mild brain injury (mean age 53.0±4.4). Clinical evaluation of patients by neuroimaging (CT, MRI, arteriography, Doppler ultrasonography, EEG), detailed physical and neurologic examination and laboratory tests was performed. Patients with TIA were characterized by contra lateral weakness, dysphasia, transient blurring of vision or blindness, abnormal pulsation of the common carotid arteries, microemboli confined to the ipsilateral retina. Untreated patients with pre-stroke demonstrated altered state of consciousness, severe headache, nausea and vomiting, visual disturbances, and focal neurological deficit, with some patients experiencing seizures.

The N-Score rating scale reported in "MCA Infarction" (Orgogozo, 1986) was used for evaluating the neurologic deficit in patients with acute cerebral stroke. The total score of acute cerebral stroke clinical manifestation differentiated severe patients (n=9, 11-35 scores) from patients with mild (n=12, 36-55 scores) and moderate patients (n=10, 60-90 scores). Most patients with acute cerebral ischaemia (61.3%) suffered ischemia in the carotid artery of left hemisphere. Arterial hypertension and cerebral atherosclerosis etiologically corresponded in all patients.

The patients with ischemia were divided into groups based on the differences between TIA, pre-stroke and acute ischemic pathogenic mechanisms. The clinical diagnosis was established on the basis of routine observations which included detailed neurological examination and neuroimaging. Groups of TIA (n=9) and pre-stroke patients with chronic cerebral blood insufficiency (n=9) were identified by neurophysiological investigations.

Example 6

Detection of Glutamate and Homocysteine in the Blood of Patients

Glutamate and homocysteine content were measured by standard high performance liquid chromatography (HPLC) according to methods described (Perry I. J., Refsum H., Morris R. W., Ebrahim S. B., Ueland P. M., Shaper A. G. Lancet. 1995, 346:1395-1398; Yamamoto T., Rossi S., Stiefel M., Doppenberg E., Zauner A., Bullock R., Marmarou A. Acta Neurochir.Suppl. 1999, 75:17-19). The limits of the normal range were 165.0 µmol/L for glutamate (Table 1) and 8.0 µmol/L for homocysteine (Table 2). Elevated glutamate and homocysteine amounts were detected in the blood of patients with acute stroke. However, approximately 66% of these patients had additional risk factors indicative of atherosclerotic processes such as high cholesterol and LDL levels (Denisenko T. V., Skuliabin D., Gromov I., Cherkas Yi., Iluchina A., Dambinova S. A., 1998. Vopr. Med. Khimii. 44, 584-590, in Russian).

Abnormal glutamate and homocysteine plasma concentrations were observed more frequently in patients with TIA than in patients with acute stroke. The positive predictive efficiency of plasma glutamate for TIA patients was 56%. The positive predictive efficiency of plasma homocysteine for TIA patients was 66%. Baseline concentrations for glutamate and homocysteine are 160 umol/L and 10 umol/L, respectively. Routine treatment for TIA was found to consistently decrease the glutamate and homocysteine levels in the blood of patients (data not shown).

In patients with pre-stroke, slightly elevated levels homocysteine were observed; levels of glutamate were unchanged (Tables 1, 2). In patients with traumatic brain injury (TBI), glutamate levels were observed that were nearly twice the glutamate levels in healthy individuals; levels of homocysteine were up to 57% higher.

TABLE 1

Glutamate concentration in the blood of patients detected by HPLC

| | | | HPLC predictive value | | | |
|---|---|---|---|---|---|---|
| | Total | Glutamate | Negative | | Positive | |
| Group | N | µmol/L | N | % | N | % |
| Healthy individuals | 28 | 165.0 ± 28.2 | 19 | 67.8 | 9 | 32.2 |
| TIA | 9 | 200.0 ± 11.7 | 4 | 44.4 | 5 | 55.6 |
| Pre-stroke | 9 | 163.7 ± 10.4 | 5 | 55.6 | 4 | 44.4 |
| Acute stroke | 31 | 172.1 ± 20.6 | 13 | 41.9 | 18 | 58.1 |
| TBI | 11 | 305.0 ± 28.8 | 4 | 36.4 | 7 | 63.6 |

We also compared homocysteine concentrations in the blood of patients with TIA and pre-stroke to homocystein concentrations in the blood of patients who have had stroke onsets. We observed that homocysteine content in the blood of patients depended on stage of the stroke, but that homocysteine concentration did not correlate with the severity of the cerebral ischemia A significant decrease in homocysteine levels in patients with acute stroke was observed after emergency therapy (data not shown).

Latex agglutination was also employed to detect TIA/stroke biomarkers in the blood serum of patients. The titer of plasma glutamate determined by latex agglutination was 3.34±0.25 in the group of healthy volunteers. Homocysteine and glutamate trends observed using HPLC were similarly observed for different groups of patients observed by using the LA technique (Tables 3, 4). Thus, increased levels of glutamate and homocysteine were similarly observed in the blood of patients with TIA and acute stroke using LA.

With respect to predictive efficiency, however, LA showed a surprising improvement over HPLC. For example, the LA method improved the positive predictive efficiency of patients with TIA and acute stroke on the basis of glutamate content to more than 63% (Tables 1, 3). The negative predictive value for healthy patients was similarly improved when using the LA technique (Tables 3, 4). The predictive value of the LA technique in the group of patients with TBI was identical to the predictive value using HPLC.

TABLE 2

Homocysteine concentration in the blood of patients detected by HPLC

| | | | HPLC predictive value | | | |
|---|---|---|---|---|---|---|
| | Total | Homocysteine | Negative | | Positive | |
| Group | N | µmol/L | N | % | N | % |
| Healthy individuals | 28 | 8.0 ± 1.7 | 20 | 71.4 | 8 | 28.6 |
| TIA | 9 | 10.8 ± 1.3 | 3 | 33.3 | 6 | 66.4 |
| Pre-stroke | 9 | 9.0 ± 1.2 | 4 | 44.4 | 5 | 55.6 |
| Acute stroke | 31 | 11.5 ± 1.1 | 11 | 35.5 | 20 | 64.5 |
| TBI | 11 | 12.6 ± 2.1 | 4 | 36.4 | 7 | 63.6 |

TABLE 3

Detection of glutamate in the blood of patients by latex agglutination

| | | | LA predictive value | | | |
|---|---|---|---|---|---|---|
| | Total | Glutamate | Negative | | Positive | |
| Group | N | Titer | N | % | N | % |
| Healthy individuals | 28 | 3.34 ± 0.25 | 22 | 78.6 | 6 | 21.4 |
| TIA | 9 | 4.52 ± 0.38 | 3 | 33.3 | 6 | 66.4 |
| Pre-stroke | 9 | 3.57 ± 0.32 | 4 | 44.4 | 5 | 55.6 |
| Acute stroke | 31 | 4.34 ± 0.47 | 11 | 35.5 | 20 | 64.5 |
| TBI | 11 | 5.12 ± 0.62 | 4 | 36.4 | 7 | 63.6 |

TABLE 4

Detection of homocysteine the blood of patients by latex agglutination

| | | | LA predictive value | | | |
|---|---|---|---|---|---|---|
| | Total | Homocysteine | Negative | | Positive | |
| Group | N | Titer | N | % | N | % |
| Healthy individuals | 28 | 2.23 ± 0.21 | 21 | 75.0 | 7 | 25.0 |
| TIA | 9 | 3.95 ± 0.37 | 3 | 33.3 | 6 | 66.4 |
| Pre-stroke | 9 | 2.89 ± 0.12 | 4 | 44.4 | 5 | 55.6 |
| Acute stroke | 31 | 4.01 ± 0.41 | 10 | 32.3 | 21 | 67.7 |
| TBI | 11 | 4.74 ± 0.38 | 4 | 36.4 | 7 | 63.6 |

Example 7

The detection of NR2A-B in the Blood of Patients

The excessive activation and damage of NMDA receptors is the result of glutamate, aspartate and homocysteine neurotoxicity. Autoantibodies to have been detected in previous work in the blood of patients with TIA and pre-stroke, supporting our hypothesis that cerebral ischemia causes neuronal damage and the appearance of autoantibodies to NMDA receptor subunits (Gusev E. I., Skvortsova V. I., Alekseev A. A., Izykenova G. A., Dambinova S. A. S. S Korsakov's J.Neurol.& Psych. 1996, 5:68-72; Dambinova S. A., Izykenova G. A. J.High Nervous Activity. 1997, 47: 439-446).

The titer of NR2A-B receptor peptides in the blood of healthy volunteers determined by LA was 2.63±0.92. Using the LA technique, we observed an increase in the test efficiency in the group of healthy persons up to 89% (Table 5). We also observed an improvement in the sensitivity of the LA test over ELISA. For example, patients with pre-stroke had slightly increased levels of NR2A-B receptor peptides over healthy volunteers when tested by ELISA, but had nearly double the level of NR2A-B receptor peptides when measured by LA (Table 5, 6). We detected high levels of NR2A-B receptor peptides using both ELISA and LA in the blood of patients with TIA and acute stroke, and observed comparable levels of predictive efficiency for each test.

Patients with TIA received routine treatment to improve brain circulation. Upon receiving treatment, NR2A-B levels decreased to levels corresponding to those observed for the healthy individuals as the patient's state normalized. As mentioned earlier, glutamate and homocysteine contents also decreased during treatment, but it never reached the levels observed in healthy individuals.

TABLE 5

Detection of NR2A-B receptor peptides in the blood of patients by latex agglutination

| | | | LA predictive value | | | |
|---|---|---|---|---|---|---|
| | Total | NR2A-B | Negative | | Positive | |
| Group | N | Titer | N | % | N | % |
| Healthy individuals | 28 | 2.63 ± 0.92 | 25 | 89.3 | 3 | 10.7 |
| TIA | 9 | 7.34 ± 0.43 | 2 | 22.2 | 7 | 77.8 |
| Pre-stroke | 9 | 4.21 ± 0.26 | 2 | 22.2 | 7 | 77.8 |
| Acute stroke | 31 | 5.20 ± 1.71 | 4 | 9.7 | 27 | 87.1 |
| TBI | 11 | 3.99 ± 0.44 | 2 | 18.8 | 9 | 81.8 |

Completely different profiles of NR2A-B were revealed in the blood of patients with acute ischemic stroke. In the blood of patients (n=8) with severe cerebral ischaemia (30.4±3.2 Orgogozo scores) NR2A-B receptor peptides titer was 4 times higher than that for control group of healthy individuals. The peptides titer for patients with mild to moderate ischemic stroke (n=22, 49-62 Orgogozo scores) was slightly elevated in comparison with those with TIA. The tendency of slight decreases in NR2A-B receptor peptide levels was observed to the end of 30 days of patients' routine treatment, correlating with improvement in the neurological state.

TABLE 6

Detection of NR2A-B receptor peptides in the blood of patients by ELISA

| | | | ELISA assay results | | | |
|---|---|---|---|---|---|---|
| | Total | NR2A-B | Negative | | Positive | |
| Group | N | Ng/ml | N | % | N | % |
| Healthy individuals | 28 | 18.2 ± 2.1 | 20 | 71.4 | 8 | 28.6 |
| TIA | 9 | 66.6 ± 4.1 | 2 | 22.2 | 7 | 77.8 |
| Pre-stroke | 9 | 23.7 ± 1.9 | 3 | 33.3 | 6 | 66.7 |
| Acute stroke | 31 | 73.4 ± 6.5 | 5 | 16.1 | 26 | 83.9 |
| TBI | 11 | 54.3 ± 4.9 | 3 | 27.3 | 8 | 72.7 |

It is necessary notice that efficiency of both laboratory assays to detect the NR2A-B receptor peptides in the blood of patients with TIA/stroke and traumatic brain injury have been determined as 78 and 82% correspondingly.

The simultaneous detection of all brain damage biomarkers: glutamate, homocysteine and NR2A-B receptor peptides in the blood patients by latex agglutination allowed to diagnose rapidly TIA/stroke with efficiency up to 85-89%. The simultaneously increased levels of all biomarkers in the blood reflect the neurological deficit and may be used also for prognosis of diseases outcome. The relation between these biomarkers is showing the degree of thromboembolic and neurotoxicity involvement in brain processes underlying the ischemia. That fact is very important for choosing the strategy of emergency therapy in short time.

Using the latex agglutination technique allowed us significantly cut off the time of blood analysis from 3-8 hours in ELISA or HPLC to 30 min in LA. This RMP semi-quantitative test demonstrated the fast, simple for interpretation and reliable data.

Example 8

Identification of cDNA Sequence Encoding Antigenic Determinants of NMDA Receptors It was necessary to first determine the cDNA sequence coding the immunological fragment of NMDA receptors responsible for the appearance of autoantibodies appearance. To find the most active peptide fragment of NMDA receptors a standard molecular biology procedure was used. Immunopositive phage GT11 containing cDNA coding NMDA receptors was isolated from a human cDNA library using autoantibodies to NMDA receptors isolated from blood samples of patients with severe cerebral ischemia or polyclonal antibodies to the NR2A receptor. An E. coli bacterial system was employed to express the phage GT11 cDNA (600 bp). The expression product was transferred to a MBmp11 vector and a restriction map was constructed by use of a standard restrictases' kit. Three unique sites of the cDNA fragment (PstI, BamHI, and PsaI) were revealed, and the 5'-3' oligonucleotide sequence orientation using KpnI, BamHI and EcoRI was deduced. The oligonucleotide (target cDNA) obtained was sequenced and compared to the sequence of the NR2A glutamate receptor (SEQ ID NO: 5) from the NCBI library. The target cDNA corresponded to the N-terminal domain of the NR2A receptor (620 bp) of SEQ ID NO: 6, namely SEQ ID NO: 7. Primers for this target nucleotide were designed. All the oligonucleotides were prepared by the phosphoramidite method on an Applied Biosystem 394 synthesizer and were purified by reverse-phase high-pressure liquid chromatography (HPLC). The oligonucleotides used for detection and capture were synthesized with an amine arm at the 5' end.

Example 9

PCR Analysis of Blood Serum Specimens

Blood samples (5 ml collected by venipuncture) from patients with TIA and pre-stroke (n=30) were collected according to standard clinical protocol and examined at the Department of Neurology of Human Brain Institute, St. Petersburg Russia. The blood specimens were used for total DNA isolation or applied on FTA paper circles.

The quantitative analysis of NR2A cDNA expression in the serum samples is basically a three step process: Total DNA isolation and purification from sera of individuals; specific cDNA coding NR2A receptor amplification; and product analysis.

The total DNA isolated by DNAzol (Mol.Res.Center, Inc., Cincinnati, Ohio) or bound on FTA blood staining collection cards (Life Technologies, Inc., Gathersburg, Md.) serves as a template for the polymerase chain reaction (PCR). In the first variant, the PCR assay uses a set of specially designed primers (50 pmol), immobilized on solid matrix of microplates and amplifies a specific cDNA sequence (620 bp) coding the NR2A glutamate receptor. In a second variant, the PCR assay uses a master ready-to-use buffer and amplifies cDNA bond on FTA paper. Following amplification, the quantity of a product is determined by enzyme or non-enzyme color reaction with a substrate.

Using the DNAzol reagent for DNA isolation, the whole blood of each individual (0.5 ml) was combined with 1 ml DNAzol (Mol.Res.Center, Inc., Cincinnati, Ohio) for 5 min at room temperature and lysed (Mackey K. et al. Mol.Biotechnol. 9: 1-5 (1997). The organic phase (0.4 ml) of each sample was transferred to a clean tube and 0.4 ml isopropanol was added. The mixture was incubated for 5 min at room temperature and centrifugated at 6,000 g for 6 minutes. The pellet was washed in 0.5 ml DNAzol and centrifugated at the same conditions. The total DNA pellet was mixed with 1 ml of 75% ethanol and centrifugated at 6,000 g for 5 minutes. Then the DNA pellet was diluted in 200 l of 8 mM NaOH and incubated at room temperature for 5 min followed by vortexing. Alkaline DNA solution was then neutralized with 160 l of 0.1 M HEPES, pH 7.4.

Immobilization of oligonucleotide probes (primers, SEQ ID NO: 8) was performed as follows. A total of 100 l of 3×PBS buffer containing the primers (150 nM) was dropped into each well of a 96-well microtiter plate (Fisher Sci., Suwanee, Ga.). After incubation for 2 h at 37° C. or overnight at room temperature, the plate was washed three times with 1×PBS buffer containing 0.05% (w/vol) Tween 20. The oligonucleotide-coated plates were stable for 2 months at 4° C.

Direct PCR reactions were performed in a final volume of 50 l (Sisk R B. in book: Molecular diagnostics: for the clinical laboratorian. Ed. by Coleman W B., and Tsongalis G J. Humana Press Inc., Totowa, N.J. 1997, pp.103-121). The total DNA (5 l), isolated from blood samples of individuals, to oligonucleotide-coated plate in duplicates and 45 l of master ready-to-use buffer containing 1 l TaKaRa Z-Taq DNA polymerase (TaKaRa Biomedicals, Otsu, Shiga, Japan) 10 l AMV/ Tfl 5× reaction buffer, 1 l dNTP mix (Promega, Madison, Wis.) 2 l of 25 mM $MgSO_4$ were added and sealed. The 30-thermal cycles (98° C. −5 s, 66° C. −2 sec ) amplification using programmable Gene Cycler thermocycler (Bio-Rad Lab., Hempstead, UK) for 20 minutes was performed. Then 50 l of PicoGreen reagent (Mol.Probes, Inc., Eugene, Oreg.) were added to each PCR products and mixed on a shaker (BioTechniques 20:676 (1996). Samples were incubated 5 min at room temperature, protected from light. After incubation the fluorescence of the samples was measured using a fluorescence microplate reader (Mol.Device, Sunnyvale, Calif.) and standard fluorescein wavelengths (excitation 480 nm, emission 520 nm). The fluorescence value of the reagent blank was subtracted from that of each of the samples, and the data was employed to generate five-point standardization curves of fluorescence versus DNA concentration, from 25 pg/ml to 25 ng/ml reaction of control target cDNA (50 ng/ml stock) with the same Pico Green reagent.

The other method of total DNA isolation is follows. Whole blood was spotted onto FTA paper and lysed, and samples of DNA immobilized within the matrix of the stain card were punched into a 3 mm (⅛") diameter paper (1 mm or 2mm Harris Micro-Punch™) and amplified directly by the amplification mix (Mackey K. et al. Mol.Biotechnol. 9:1-5 (1997).

The FTA Bloodstain Card is divided into 4 circles for at least 4 different 120 l samples of EDTA collected whole blood. Samples of blood were dried at room temperature for at least 1 hour. A circle was drawn with a #2 pencil around each blood to visualize where the blood had been spotted after the FTA paper processing. The FTA Bloodstain Card was then placed in a small plastic tray and 50 ml of FTA Purification Reagent was added and incubated on a shaker for 5 minutes. FTA Purification Reagent was replace 3 times with 25-50 ml of the fresh solution and shaken for an additional 5 minutes. Then 25-50 ml of TE4 (10 mM Tris-HCl pH 8.0; 0.1 mM EDTA pH 8.0) was added and the mixture incubated twice on a shaker for 5 minutes. The FTA Bloodstain Card was allowed to air dry completely during 2 hours at room temperature. The samples were then punched from the cards using a 3 mm diameter punch or the Harris Micro-Punch (1.2 mm or 2.0 mm), and transferred into corresponding microplate wells. PCR was then performed using the above-described procedure using regular PCR microplates and a ready-to-use buffer containing primers.

Patients (n=30, the age of 44-77) were divided into two groups. The first group of patients (n=12) were diagnosed with TIA in the carotid circulatory system, according to the following neurological criteria. Neural dysfunction was localized to a specific vascular distribution; the duration of the attack was usually less that 15 minutes and never exceeded 24 hours; and the patients did not have abnormal neurologic signs between attacks. The second pre-stroke group (n=18) were diagnosed with TIA in the vertebral-basilar circulatory system. The second group of patients was subdivided on the basis of compensation or non-compensation of neurological deficit. The third group (n=12) included patients with migraine and epilepsy.

The control group of healthy individuals (n=20) showed a level of NR2A cDNA expression of 1.2 0.11 pg/ml. The first group demonstrated slightly elevated levels of NR2A cDNA expression of 1.7 0.13 pg/ml. The patients with compensation of neurological deficit from the second group showed a level of NR2A cDNA expression of 1.8 1.4 pg/ml. At the same time, the patients without compensation of neurological deficit that possessed more severe symptoms of TIA showed levels of NR2A cDNA expression of 3 times the levels seen in healthy individuals. Patients suffering migraine and epilepsy did not show any increase of NR2A cDNA expression when compared with the control group.

Example 10

Immunological Analysis of Blood Serum Specimens

Blood samples (10 ml, collected by venipuncture) from patients with cerebral ischemia (n=70), and healthy individuals (n=200), collected according to standard clinical protocols, were examined at the Neurology Hospital of Russian Medical Academy (Moscow, Russia). The blood specimens were centrifugated (4000 g, 5 min, +4° C.) and the collected serum stored at −70° C. for further analysis.

Computer analysis was employed to predict the antigenic determinants in the NR2A receptor protein structure based on hydrophobicity profile (Hopp, T. P. and K. R. Woods, *Proc. Natl. Acad. Sci. USA* 6:3824-3828 (1981)) and antigenicity (Welling, G. W., et al., *FEBS Lett.* 188:215-218 (1985)). Based upon this analysis, the N-terminal sequence of the NR2A NMDA receptor was synthesized. This synthetic peptide, which corresponded to amino acid sequence (494-514) (Grandy, D K., et al., *Proc. Natl. Acad. Sci. U.S.A.* 86:9762-9766(1989) (SEQ ID NO: 3) of human NR2A NMDA, was produced by solid-phase synthesis in a NPS-400 semi-automated synthesizer (Neosystem Lab, France) on MBHA resin using the BOC/Bzl strategy for the first two amino acids. The peptides were purified by preparative HPLC on a DELTAPAC™C18 column (Waters Chromatography, Milford, Mass.) in a $H_2O$/acetonitrile/0.015 TFA system. The purity of the peptides was determined by analytical HPLC and ranged from 90% to 98%. The peptide sequence was verified by amino acid analysis after acid hydrolysis. This peptide was used in immunoassays of blood serum from patients and healthy individuals.

A quantitative analysis of the level of NR2A autoantibodies in serum samples was performed by enzyme-linked immunosorbent assay (ELISA) (Ngo, T. T. and H. M. Lenhoff, *FEBS Lett.* 116:285-288 (1980)). The diluted blood sera (1:50) and polyclonal antibodies to the NR2A peptide as a standard (0.01 ng/ml-400 ng/ml) were applied to the immunosorbent. The plate was incubated for 1 h at 25° C. and then washed by 0.05 M phosphate buffer, pH 7.4, containing 0.05% of TWEEN-20™. Rabbit antibodies to the human immunoglobulin labeled with horseradish peroxidase were added (Sigma, St. Louis, Mo.; 1:1000), and the plate was incubated for 1 h at 25° C. After incubation the wells were washed twice in the same buffer. The reaction was revealed by o-phenylenediamine in 0.05 M citrate buffer, pH 4.3 monitored at 490 nm on a microplate reader (BioRad, UK). The titer of NR2A autoantibodies in blood serum was determined by ELISA using a standard curve of the absorbence units of NR2A autoantibodies versus their concentration in a microtiter well plate.

The synthetic peptide corresponding to the NR2A NMDA glutamate receptors (3 μg) were immobilized on a nitrocellulose membrane (0.45 μm, Shleicher-Shuell, Germany) in phosphate-buffered saline (PBS), pH 7.4, then washed 2-3 times in the same buffer. Membranes with immobilized peptide were incubated with the diluted serum (1:50) of cerebral ischemia patients and other subjects for 1 h at 25° C., and then rinsed 4 times with the PBS buffer. Secondary rabbit anti-human immunoglobulins conjugated with horseradish peroxidase (Sigma, St. Louis, Mo.; 1:1000) were incubated with the membrane for 1 h at 25° C., then washed 4 times with PBS. The development of brown color was registered and then quantitated by densitometry.

To provide a positive control or standard, rabbit polyclonal antibodies were raised against NR2A synthetic peptide corresponding to amino acid sequence predicted from the cloned human NR2A protein (Science 256:1217-1221 (1992); SEQ ID NO: 1). For glutaraldehyde conjugation, 10 mg of peptide and 40 mg of human serum albumin (Sigma, St. Louis, Mo.) were incubated for 1.45 h at room temperature in 4 ml of PBS containing 5% glutaraldehyde. The reaction was stopped by adding glycine to a final concentration of 0.2 M, and the conjugate was dialyzed against PBS. Rabbits were given initial injections of 1 mg of conjugated peptide in complete Freund's and subsequent injections of 0.5 mg of peptide in incomplete Freund's adjuvant at successive 2 week intervals. Antibodies were affinity purified according standard procedure (Warr, G. W., Purification of antibodies, In: *Antibody as a Tool*, Eds., Marchalonis, J. J., and G. W. Warr, J. Wiley, UK, pp. 59-96 (1982)) and were shown to be selective for the NR2A NMDA glutamate receptor using Western blot analysis.

The patients (men, n=30; women, n=40; age of 40-75) were admitted in the hospital within no more than six hours after the onset of an ishemic episode. All patients were divided into three groups according to the severity of the stroke: The first group had moderate ischemic stroke (n=25), manifested by moderate focal deficit (>60-Orgogozo scale). The second group had severe stroke (n=30), manifested by mild disorders of consciousness, severe headache, meningeal sings, and pronounced focal deficit (30-60 -Orgogozo scale). The third group had extremely severe stroke (n=15), accompanied by stupor-coma, signs of brain edema, autonomic dysfunction, and severe focal deficit (<30 -Orgogozo scale).

The level of NR2A autoantibodies was measured in the blood serum of healthy persons (n=200; age 35-75) as a control, and ranged from 0.3-1.5 ng/ml. The NR2A autoantibody level in the 55 patients of the first and second groups was significantly greater than that in the control group ($p<0.01$). Levels of NR2A autoantibodies were monitored every three hours during the first day, and then up to 5th day after stroke. The level of NR2A autoantibodies in the blood serum of patients with severe stroke was significantly higher than that in the blood serum of patients with moderate stroke, especially in the 9-12 hours after the onset of a stroke ($p<0.05$). The tendency for NR2A autoantibodies level to decrease to the control level on the first day of stroke was registered in group of patients with good neurological recovery (90,50,5 units on Orgogozo scale). It can be concluded that the dynamic changes in NR2A autoantibodies level may predict a recovery period of patients after ischemic stroke.

Example 11

SPRIA Assay of Autoantibodies

The solid-phase radioimmunoassay (SPRIA) of autoantibodies is performed as follows: a 10% acetic acid solution is added for one minute to the Cooker microtiter microplates (available from Dynatech Co., USA) for activation, whereupon 0.1 ml of the blood serum under analysis (diluted 1:40) is applied to the microplates and subjected to incubation for four hours at 25° C. Then the microplate are washed with a 0.14 M sodium chloride solution and 0.1 ml of a mixture of the respective fragment of the mammal's brain protein labeled by 125I in the presence of nonlabelled one. The plates are incubated for 20 hours at 4° C. On completion of incubation, the microplates are washed with a 0.14M sodium chloride solution, after which each of the wells of the microplates is cut off and placed in gamma-counting vials.

Example 12

ELISA Assay of Autoantibodies

The enzyme-linked immunosorbent assay (ELISA) of autoantibodies is carried out as follows: the samples of the blood serum diluted 1:40 or 1:50 are applied to the respective immunosorbent. Then the plate carrying the immunosorbent is incubated for 30 min at 37° C., whereupon the wells of the plate are washed with a 0.05 M phosphate buffer, containing 0.05% of Tween-20. Rabbit antibodies to human immunoglobulin labeled with horseradish peroxidase (conjugate) are added thereto, and the plate is reincubated for 35 min at 37° C., then washed by the aforementioned buffer and distilled water. The reaction with conjugate is determined by adding chromogen, i.e., orthophenylenediamine in the presence of 30% hydrogen peroxide. The intensity of color development is evaluated by using the rider (available Multiskan microplate rider) at the 492 nm wavelength.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for aiding in the differential diagnosis of ischemic versus hemorrhagic stroke comprising:
   a) obtaining a test sample of blood, plasma or serum from a human subject at the time said subject is suspected of suffering from an ischemic or hemorrhagic stroke;
   b) analyzing the obtained test sample for the amount of (i) NR2A N-terminal domain fragment peptide having SEQ ID NO: 3 and NR2B N-terminal domain fragment peptide having SEQ ID NO: 12 (NR2A-B receptor peptides) or (ii) NR2 antibody that binds NR2A N-terminal domain fragment peptide having SEQ ID NO: 3;
   c) comparing the result of step (b) with a corresponding reference amount of said NR2A-B receptor peptides or NR2 antibody, or a combination thereof, wherein the corresponding reference amount is derived from a population of apparently healthy human subjects; and
   d) if the amount determined in step (b) exceeds the corresponding reference amount, diagnosing said human as having an increased probability of having an ischemic stroke over hemorrhagic stroke.

2. The method of claim 1 wherein the amount of said NR2A-B receptor peptides is measured.

3. The method of claim 1 wherein the amount of said NR2 antibody is measured.

4. The method of claim 1, wherein step (a) occurs within three hours of the onset of symptoms of TIA or stroke.

5. The method of claim 1 wherein the amount of time elapsed between step (b) and step (c) is less than about one hour.

6. The method of claim 1 wherein the NR2A-B receptor peptides or NR2 antibody is measured by immunoassay.

7. The method of claim 1 wherein the NR2A-B receptor peptides or NR2 antibody is measured by agglutination comprising:
   a) contacting the test sample with:
      i) poly- or monoclonal antibodies bound on an agglutinating carrier for sufficient time and under conditions to promote agglutination, wherein the antibodies are specific for NR2A-B receptor peptides; or
      ii) said NR2A-B receptor peptides bound on an agglutinating carrier for sufficient time and under conditions to promote agglutination between the NR2A-B receptor peptides and NR2 antibody in said test sample; and
   b) measuring a signal generated from the agglutination; and c) correlating the strength of said signal to the titer of NR2A-B receptor peptides or NR2 antibody present in said sample.

8. The method of claim 7, wherein the sufficient time period is 30 minutes or less.

9. The method of claim 7 wherein the carrier comprises polysterene latex beads having a mean diameter of from about 0.25 to about 0.4 µm.

10. The method of claim 1 wherein levels of NR2A-B receptor peptides or NR2 antibody are measured by a process comprising:
   a) contacting the test sample with NR2A-B receptor peptides or NR2 antibody capture agent for a time sufficient and under conditions to form a complex between said NR2A-B receptor peptides or NR2 antibody capture agent and NR2A-B receptor peptides or NR2 antibody in said test sample;
   b) contacting the complex with an indicator reagent comprising a secondary antibody attached to a signal generating compound;
   c) measuring the signal; and
   d) correlating the strength of said signal to the titer of NR2A-B receptor peptides or NR2 antibody present in said sample.

11. The method of claim 1, wherein said step (b) comprises immunochemically analyzing said obtained test sample in an immunoassay, and said corresponding reference amount in step (c) is immunochemically derived using the same immunoassay in step (b).

* * * * *